US012697755B2

(12) United States Patent
Di Maio et al.

(10) Patent No.: US 12,697,755 B2
(45) Date of Patent: **\*Aug. 4, 2026**

(54) PROCESS FOR PREPARING LAYERED FOAMED POLYMERIC MATERIALS

(71) Applicant: MATERIAS S.r.l., Naples (IT)

(72) Inventors: Ernesto Di Maio, Naples (IT); Luigi Nicolais, Ercolano (IT)

(73) Assignee: MATERIAS S.r.l., Naples (IT)

( * ) Notice: Subject to any disclaimer, the term of this patent is extended or adjusted under 35 U.S.C. 154(b) by 1403 days.

This patent is subject to a terminal disclaimer.

(21) Appl. No.: 17/047,486

(22) PCT Filed: Jan. 4, 2019

(86) PCT No.: PCT/IB2019/050068
§ 371 (c)(1),
(2) Date: Oct. 14, 2020

(87) PCT Pub. No.: WO2019/202407
PCT Pub. Date: Oct. 24, 2019

(65) Prior Publication Data
US 2021/0114266 A1 Apr. 22, 2021

(30) Foreign Application Priority Data

Apr. 19, 2018 (IT) ........................ 102018000004727

(51) Int. Cl.
| | |
|---|---|
| *B29C 44/34* | (2006.01) |
| *A61L 27/18* | (2006.01) |
| *A61L 27/34* | (2006.01) |
| *A61L 27/50* | (2006.01) |
| *B29C 44/06* | (2006.01) |
| *C08J 9/00* | (2006.01) |
| *C08J 9/12* | (2006.01) |
| *C08J 9/14* | (2006.01) |
| *B29K 25/00* | (2006.01) |
| *B29K 67/00* | (2006.01) |

(52) U.S. Cl.
CPC .......... *B29C 44/3453* (2013.01); *A61L 27/18* (2013.01); *A61L 27/34* (2013.01); *A61L 27/50* (2013.01); *B29C 44/06* (2013.01); *B29C 44/348* (2013.01); *C08J 9/0061* (2013.01); *C08J 9/122* (2013.01); *C08J 9/146* (2013.01); *A61L 2420/02* (2013.01); *A61L 2430/02* (2013.01); *A61L 2430/24* (2013.01); *A61L 2430/38* (2013.01); *B29K 2025/06* (2013.01); *B29K 2067/00* (2013.01); *C08J 2203/06* (2013.01); *C08J 2203/142* (2013.01); *C08J 2203/182* (2013.01); *C08J 2207/10* (2013.01); *C08J 2325/06* (2013.01); *C08J 2367/04* (2013.01); *C08J 2429/04* (2013.01)

(58) Field of Classification Search
CPC .......... A61L 27/18; A61L 27/34; A61L 27/50; A61L 2420/02; A61L 2430/02; A61L 2430/24; A61L 2430/38; B29C 44/06; B29C 44/3453; B29C 44/348; B29K 2023/00; B29K 2025/06; B29K 2067/00; B29K 2075/00; B29K 2077/00; C08J 9/0061; C08J 9/112; C08J 9/141; C08J 9/146; C08J 9/18; C08J 9/34; C08J 2203/06; C08J 2203/142; C08J 2203/182; C08J 2207/00; C08J 2207/10; C08J 2300/22; C08J 2323/02; C08J 2325/06; C08J 2361/20; C08J 2363/00; C08J 2367/00; C08J 2367/04; C08J 2375/04; C08J 2377/00; C08J 2379/08; C08J 2429/04
See application file for complete search history.

(56) References Cited

U.S. PATENT DOCUMENTS

| | | | |
|---|---|---|---|
| 3,787,542 A | 1/1974 | Gallagher et al. | |
| 4,486,901 A | 12/1984 | Donzis | |
| 5,670,102 A | 9/1997 | Perman et al. | |
| 2003/0105176 A1* | 6/2003 | Haas ..................... | C08J 9/0061 521/79 |
| 2004/0198853 A1 | 10/2004 | Saito et al. | |

(Continued)

FOREIGN PATENT DOCUMENTS

| | | |
|---|---|---|
| EP | 0 610 953 A1 | 8/1994 |
| EP | 1 452 191 A2 | 9/2004 |

(Continued)

OTHER PUBLICATIONS

Japanese Office Action issued Jan. 24, 2023 in Japanese Application 2021-506079, (with unedited computer-generated English translation), 39 pages.

(Continued)

*Primary Examiner* — John M Cooney
(74) *Attorney, Agent, or Firm* — Oblon, McClelland, Maier & Neustadt, L.L.P.

(57) ABSTRACT

The present invention concerns layered foamed polymeric materials lacking discontinuities at the interface between the layers and a preparation process thereof comprising the following steps: —providing a foamable polymeric material; —solubilising said one or more foaming agents in the foamable polymeric material under pressure and at a temperature greater than 20° C.; and —releasing the pressure instantaneously; where the solubilisation step is carried out with a pressure profile of said one or more foaming agents that is variable over time.

14 Claims, 15 Drawing Sheets

(56)                  References Cited

U.S. PATENT DOCUMENTS

| | | |
|---|---|---|
| 2005/0261387 A1 | 11/2005 | Stevenson et al. |
| 2008/0281011 A1 | 11/2008 | Strauss |
| 2010/0022479 A1 | 1/2010 | Bourban et al. |
| 2015/0125663 A1 | 5/2015 | Faden et al. |
| 2015/0283432 A1 | 10/2015 | Sullivan et al. |

FOREIGN PATENT DOCUMENTS

| | | | |
|---|---|---|---|
| EP | 1 064 958 B1 | 8/2005 | |
| EP | 1 878 450 A1 | 1/2008 | |
| EP | 2 040 768 B1 | 3/2015 | |
| JP | 07-102103 A | 4/1995 | |
| JP | 2001-49018 A | 2/2001 | |
| JP | 2003-49018 A | 2/2003 | |
| JP | 2009-542890 A | 12/2009 | |
| JP | 2010-516501 A | 5/2010 | |
| JP | 2018-19679 A | 2/2018 | |
| TW | 200918316 | 5/2009 | |
| WO | WO-2006053132 A2 * | 5/2006 | ......... A61F 2/30942 |
| WO | WO 2008/089358 A2 | 7/2008 | |
| WO | WO 2014/041516 A1 | 3/2014 | |
| WO | WO 2016/102291 A1 | 6/2016 | |
| WO | WO 2019/155747 A1 | 8/2019 | |

OTHER PUBLICATIONS

International Search Report and Written Opinion issued May 20, 2019, in PCT/IB2019/050068 filed Jan. 4, 2019.

Gupta, N. et al., "Comparison of compressive properties of layered syntactic foams having gradient in microballoon volume fraction and wall thickness", Materials Science and Engineering A, vol. 427, 2006, pp. 331-342.

Wang, E. et al., "The blast resistance of sandwich composites with stepwise graded cores", International Journal of Solids and Structures, vol. 46, 2009, pp. 3492-3502.

Zhou, C. et al., "Fabrication of functionally graded porous polymer via supercritical $CO_2$ foaming", Composites: Part B, vol. 42, 2011, pp. 318-325.

* cited by examiner

Fig. 8
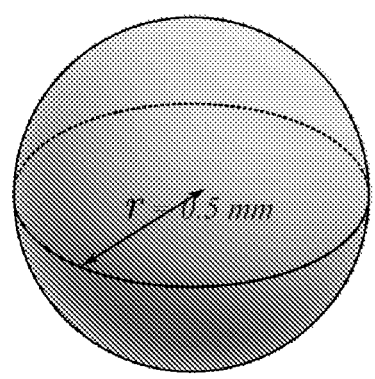
Fig. 8A
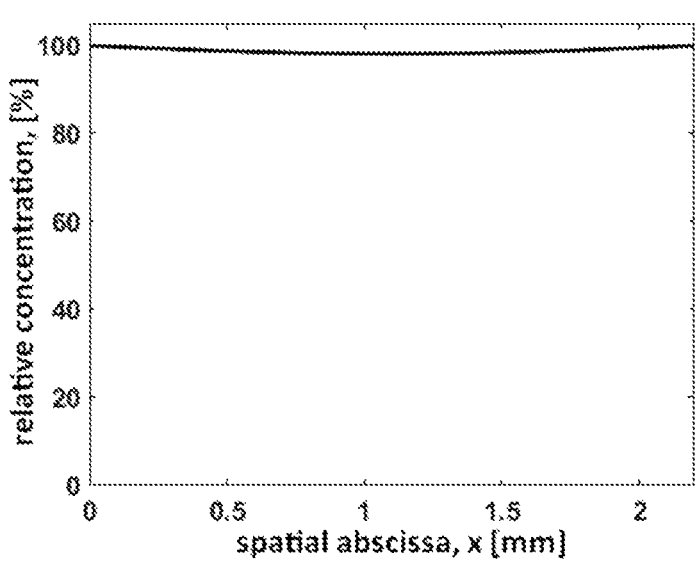
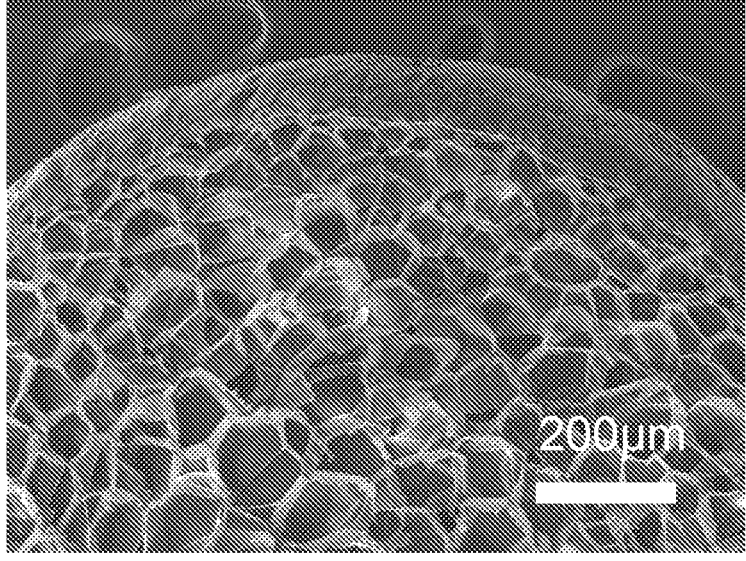
Fig. 8B

PROCESS FOR PREPARING LAYERED FOAMED POLYMERIC MATERIALS

CROSS REFERENCE TO RELATED APPLICATIONS

This application is a 371 of International Patent Application No. PCT/IB2019/050068, filed on Jan. 4, 2019, and claims priority to Italian Patent Application No. 102018000004727, filed on Apr. 19, 2018, both of which are incorporated herein by reference in their entireties.

FIELD OF THE INVENTION

The present invention concerns a process for preparing layered foamed polymeric materials, both in terms of cell morphology and in terms of density.

In particular, the process uses a procedure for the solubilisation of physical foaming agents, necessary for the subsequent foaming, characterised by variable conditions over time. More specifically, the variable conditions over time of the solubilisation step generate non-uniform profiles of the concentrations of the physical foaming agents in the polymer, which, upon foaming, generate correspondingly non-uniform morphologies and densities.

BACKGROUND

Recently there has been an interest in "gradient" foamed materials, whose structural and functional properties are improved with respect to foamed materials characterised by uniform structures in terms of cell density and/or morphology. This has been demonstrated through recent scientific studies, both theoretical-numerical and experimental. The patent literature describes the use and advantage of such layered foamed structures or those with gradient morphology and/or density. The publication of patent application no. US2015125663 describes the use of different layers of polymer foams, assembled in a "gradient" manner, in the absorption of energy from impact in helmets.

Another area in which layered foams are of interest is that of expansion for sintering (also known as steam-chest moulding or bead-foaming), which is very common in the production of sintered foamed polystyrene products, but more recently also using, among others, polypropylene, thermoplastic polyurethane and polylactic acid. In this field, pre-foamed beads (almost spherical in shape and with dimensions nearing a millimetre) are used which, in the manufacture of a product, are inserted into a mould and covered with water vapour or hot gases to achieve the final foaming and sintering of the beads. The final foaming is mainly due to foaming agents, for example pentane, which are still contained in the pre-foamed bead and evolve with heating.

Indeed, the possibility of preventing the loss of the foaming agent via diffusion in the period between pre-foaming and final foaming is of significant technological importance. This loss by diffusion phenomenon is a limit in terms of the conservation of the pre-foamed beads and a process standardisation issue, when products must be produced with beads that have been subject to a different conservation period (seasoning).

Having a pre-foamed bead available with a radially layered morphology, for example with a dense intermediate or external layer, which acts as a barrier to prevent the loss of the foaming agent in the inner layers, would solve the aforementioned problem.

Some commercial products, such as golf balls or sports impact protection devices, are layered products with one or more foamed layers (see, for example, Sullivan et al., US 2015/0283432 and Donzis, U.S. Pat. No. 4,486,901).

The technologies adapted to create such stratified structures, however, appear artificial, long and/or difficult to industrialise.

For example, Nikhil Gupta et al., in "Comparison of compressive properties of layered syntactic foams having gradient in microballoon volume fraction and wall thickness" Mater. Sci. Eng A 427 (2006) 331-342, describe a laboratory strategy that involves placing hollow glass microspheres with different dimensions in the polymer.

In European patent applications EP1452191A2 and EP1878450A1, procedures are described for the creation of layered structures via the use of composite materials. In particular, in EP1452191A2 mixtures of two polymeric materials are used with a concentration gradient varying from a step mainly constituted by a first material to a step mainly constituted by a second component, and in EP1878450A1 composite preforms are made using the precise positioning of fillers and/or fibres in a mould together with a foamable polymeric material. These procedures require both the use of composite materials and a complex preparation and distribution of the components of these materials.

More frequently the coupling, by means of bonding or welding, of several layers of foams with different morphologies and/or densities is described and used, as described in WO2016102291A1, WO2014041516A1 and TW200918316, and by Erheng Wang et al., in "The blast resistance of sandwich composites with stepwise graded cores" International Journal of Solids and Structures 46 (2009) 3492-3502. Aside from the laboriousness of the coupling procedures, it should be noted that these, especially when executed by means of bonding or heat-welding, have a discontinuity at the junction which is a problem in terms of performance and design. Another approach was introduced by Zhou C. et al., in "Fabrication of functionally graded porous polymer via supercritical $CO_2$ foaming", Composites: Part B 42 (2011) 318-325, and considers the use of "profiles of non-equilibrium of the concentration of the foaming agent". In this method, the material to be foamed has been partially saturated by the foaming agent through a solubilisation step, which takes place at a constant temperature and pressure over time, shorter than that which is necessary to achieve a uniform concentration of the foaming agent. In this case, the most remote portions (with respect to the free surfaces in contact with the foaming agent under pressure, thus the innermost portions) of the samples to be foamed contain a lower concentration of the foaming agent with respect to the portions adjacent to said surfaces (more external portions), in which the concentration of the foaming agent readily reaches equilibrium conditions with the foaming agent's external pressure. As a result, the internal portion of the sample will be less foamed or lack foam, while the outer portions will be completely foamed.

The design of such structures presupposes knowledge of the diffusion coefficient of the foaming agent in the polymer, available for a large number of polymer/foaming agent systems.

Although the process described is simple to manufacture, it is rather limited, as it only allows the construction of single-gradient foamed materials, characterised by less foamed layers inside the sample and more foamed layers outside. The symmetries of the gradient clearly depend on the sample shape and which sample surfaces can be accessed by the foaming agent.

SUMMARY OF THE INVENTION

The process of the present invention aims to overcome the disadvantages of the methods known in the art.

In particular, the Applicant has observed that with the process of the present invention, layered foamed structures can be obtained with a simple, low-cost process.

Moreover, the Applicant has observed that the layered foamed structures obtained with the process of the present invention do not present discontinuities at the interface between the layers, but on the contrary show a gradual variation of both the density and morphology of the bubbles present in the foamed material.

The Applicant has also observed that the process of the present invention makes it possible to obtain layered foamed structures with a wide choice of design, both in terms of number of layers, and of their morphology and density.

The Applicant has observed that these and other advantages can be obtained by means of a process for preparing layered foamed materials which comprises at least one step of non-equilibrium in the mass transport of a foaming agent in a polymer using at least one variable condition over time in the solubilisation step before the foaming.

The Applicant has observed that the use of one or more variable conditions over time in the solubilisation step of one or more foaming agents in a polymer generate non-uniform profiles of the concentrations of the foaming agents in the same polymer, which upon foaming correspondingly generate non-uniform morphologies and densities.

The Applicant has considered that the penetration depth $L_{pen}$ in the polymer of any variation of the boundary conditions in mass transport characterised by a certain characteristic time T (as, for example, the period of a sine wave) is given by the equation (1):

$$L_{pen}=\sqrt{DT} \tag{1}$$

wherein D is the diffusivity of the foaming agent in the polymer.

If the variation of the boundary conditions in the mass transport is instantaneous, the relation itself indicates the thickness, at each time T after the imposition of the variation itself, within which the effect of the variation is relevant.

The Applicant has observed that the variation of boundary conditions in mass transport can be substantially influenced by three variables which consist of:
pressure variations
variations in the composition of the expanding gas
temperature variations The Applicant has first found that the pressure variation can be appropriately adjusted through the use of a management program capable of causing periodic variations characterised by a certain period T and by the waveform, which can be, for example, sinusoidal, triangular, square, sawtooth, and so on.

The Applicant has also found that the pressure variation can be appropriately adjusted through the use of a management program capable of operating non-periodic variations, quickly or slowly, following linear, parabolic, exponential, impulsive profiles, and so on.

Similarly, the Applicant has found that the variation in the composition of the expanding gas can be suitably adjusted by varying the partial pressures of two or more foaming agents (such as nitrogen and carbon dioxide) characterised by different diffusivities, D.

Finally, the Applicant has observed that temperature variations, whose dynamics follow those of energy transport and are characterised by other properties of the system (thermal diffusivity), can be superimposed/coupled in a calibrated manner to the dynamics of mass transport dependent on the pressure and the composition of the expanding gas to obtain different layers.

The Applicant has therefore found that, by appropriately designing the solubilisation step by means of periodic variations in the pressure of one or more foaming agents, also by using temperature variations, it is possible to obtain foamed polymers with a multi-layer structure, each layer having a specific and different morphology and density.

Therefore, a first object of the present invention is represented by a process for preparing layered foamed polymeric materials by means of the use of one or more foaming agents, where said process comprises the following steps:
providing a foamable polymeric material;
solubilising said one or more foaming agents in the foamable polymeric material under pressure and at a temperature greater than 20° C.; and
releasing the pressure instantaneously;
characterised in that the solubilisation step is carried out with a pressure profile of said one or more foaming agents that is variable over time.

A second object of the present invention is represented by a foamed polymeric material with a multi-layer structure obtained by the process according to the first object of the present invention.

A third object of the present invention is represented by a foamed polymeric material with a multi-layer structure and uniform composition, where said multi-layer structure comprises at least two layers and where each of said at least two layers has a specific and different morphology and/or density, characterised in that it presents a gradual variation in density and/or morphology at the interface between said at least two layers present in the foamed material.

In particular, the foamed polymeric material, in accordance with the third object of the present invention, is characterised in that it does not present discontinuities in morphology and/or density at the interface between said at least two layers.

A fourth object of the present invention is represented by a manufactured product made wholly or in part with a foamed polymeric material with a multi-layer structure and uniform composition, where said multi-layer structure comprises at least two layers and where each of said at least two layers has a specific and different morphology and/or density, characterised in that it presents a gradual variation in density and/or morphology at the interface between said at least two layers present in the foamed material.

BRIEF DESCRIPTION OF THE DRAWINGS

FIG. 8 shows a diagram of a sample used in examples 7-9, with radius r highlighted.

FIG. 8A shows the axial concentration profile of the foaming agent immediately prior to the release of pressure to allow the foaming used in example 7.

FIG. 8B shows a scanning electron microscope photograph of the foam section resulting from the sample subjected to the procedure of example 7 (scale bar equal to 200 μm).

DETAILED DESCRIPTION OF THE INVENTION

Figure 1A:
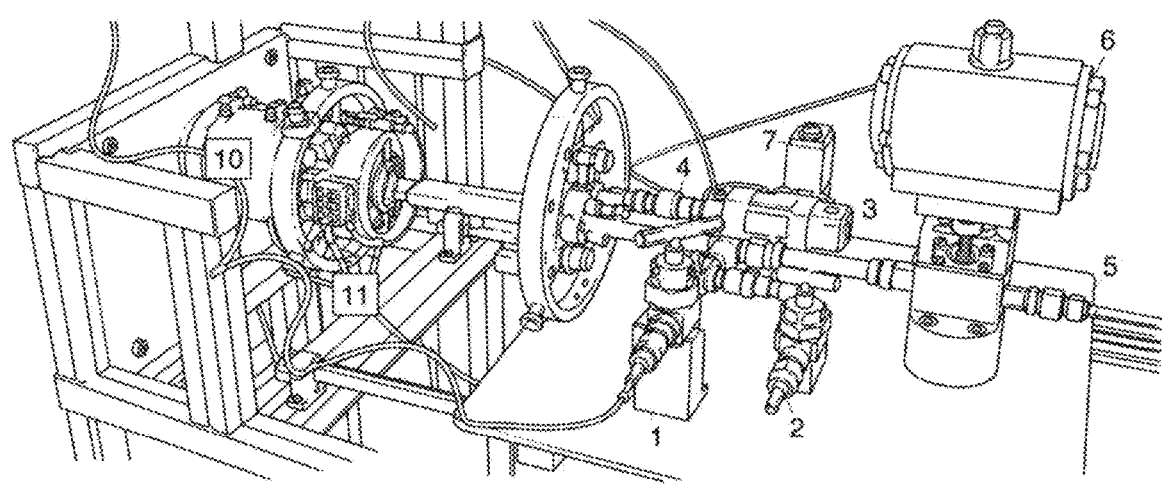
FIG. 1A shows a photograph of the discontinuous foaming apparatus used in the present invention.

The expression "polymeric material" indicates a polymeric material comprising a thermoplastic or thermosetting homo-polymer or co-polymer, or mixtures thereof.

The expression "foamable polymeric material" indicates a polymeric material capable of absorbing a foaming agent at a certain temperature and under pressure, allowing the nucleation of bubbles upon the release of the same pressure and resisting the straightening stresses during the growth of the bubbles, up to solidification.

The expression "foaming agent" indicates a substance capable of causing the expansion of the polymeric material through the formation of bubbles inside the polymeric material.

The expression "multi-layer structure" indicates a structure comprising two or more layers, preferably three or more layers.

The expression "uniform composition" indicates a composition consisting of a polymeric material of uniform and constant composition in all its points.

The term "discontinuity" indicates a net and distinct boundary between two adjacent layers, typical of composite materials made by hot junction means or with adhesives of two layers with different structures made separately.

The term "density" indicates the ratio between the weight of a given volume of a layer of polymeric material and this volume.

The term "morphology" indicates the shape, size and number of units per volume of the bubbles formed within the foamed polymeric material.

The term "foamed polymeric material" indicates a polymeric material inside which bubbles have been formed by means of a foaming agent.

A first object of the present invention is represented by a process for preparing layered foamed polymeric materials by means of the use of one or more foaming agents, where said process comprises the following steps:

providing a foamable polymeric material;

solubilising said one or more foaming agents in the foamable polymeric material under pressure and at a temperature greater than 20° C.; and releasing the pressure instantaneously;

characterised in that the solubilisation step is carried out with a pressure profile of said one or more foaming agents that is variable over time.

In accordance with the first object of the invention, said pressure profile preferably varies over time in a periodic or non-periodic manner.

In accordance with the first object of the invention, said pressure profile preferably varies over time in a periodic manner with a waveform selected from the group consisting of the sinusoidal, triangular, square or sawtooth type, or combinations thereof.

In accordance with the first object of the invention, said pressure profile preferably varies over time in a non-periodic manner following a linear, sectioned, curvilinear, parabolic, exponential, impulsive profile or combinations thereof.

In accordance with the first object of the invention, said pressure profile varies from a minimum pressure equal to atmospheric pressure to a maximum of 300 bars, more preferably from atmospheric pressure to 250 bars, and advantageously from atmospheric pressure to 200 bars.

In accordance with the first object of the invention, said pressure profile preferably comprises at least one step with an increasing pressure profile over time and at least one step with a decreasing pressure profile over time.

In accordance with the first object of the invention, said pressure profile can advantageously comprise at least one step with a constant pressure profile over time.

In accordance with the first object of the invention, the solubilisation step is carried out with a foaming agent or with a mixture of two or more foaming agents, preferably with a mixture of two foaming agents. Advantageously, the solubilisation step can be carried out by varying the concentration of the foaming agent over time. In particular, the concentration of the foaming agents of said mixture can vary over time.

In accordance with the first object of the invention, the solubilisation step is preferably carried out at a temperature comprised between 20° and 350° C., more preferably between 30° and 250° C., and advantageously between 50° and 200° C.

In accordance with the first object of the invention, said one or more foaming agents are selected from the group consisting of inert gases, carbon dioxide, and substituted or not substituted aliphatic hydrocarbons (linear, branched or cyclic), having from 3 to 8 carbon atoms. Advantageously, the foaming agent is selected from the group comprising nitrogen, carbon dioxide, n-butane, iso-butane, n-pentane, and iso-pentane. Preferably, the substituted aliphatic hydrocarbons comprise halogenated hydrocarbons, in particular chlorocarbons, chlorofluorocarbons and fluorocarbons, such as, for example, 1,1,1,2-tetrafluoroethane (Freon R-134a), 1,1-difluoroethane (Freon R-152a), difluoromethane (Freon R-32), pentafluoroethane (Freon R-125).

In accordance with the first object of the invention, said polymeric material is preferably selected from the group consisting of thermoplastic or thermosetting polymeric materials.

Advantageously, said thermoplastic polymeric materials are selected from the group which comprises polyolefins, polyurethanes, polyesters and polyamides.

Preferably, said thermosetting polymeric materials are selected from the group comprising polyurethanes, epoxy resins, melamine resins, polyphenols, and polyimides.

Preferably, said polymeric materials are polymers and copolymers of styrene, ethylene, propylene, and other olefins, such as polystyrene, polyethylene, and polypropylene. Optionally, said polymeric materials can comprise one or more co-monomers. The co-monomers can include, for example, alkylstyrenes, divinylbenzene, acrylonitrile, diphenylether, alpha-methylstyrene, or combinations thereof. By way of example, the polymeric material can comprise from about 0% by weight to about 30% by weight, preferably from about 0.1% by weight to about 15% by weight, and more preferably from about 1% by weight to about 10% by weight of co-monomer.

Preferably, the polymeric materials can have a molecular weight $M_w$ (measured by GPC) from about 10,000 Daltons to about 500,000 Daltons, more preferably from about 150,000 Daltons to about 400,000 Daltons, and even more preferably from about 200,000 Daltons to about 350,000 Daltons.

Advantageously, the polymeric materials have a sliding index, measured according to standard ASTM D 1238 at a temperature of 200° C. and a load of 10 kg, comprised between 1.0 and 20 g/10 min.

Preferably, the polymeric material used in the present invention has a uniform composition for its entire thickness, i.e. it has a uniform and constant composition in all its points.

Advantageously, the process of the present invention makes it possible to produce multi-layer products with two or more layers while avoiding the use of composite materials comprising a composition gradient as described in EP1452191A2 and EP1878450A1.

Moreover, the process of the present invention advantageously makes it possible to create multiple gradients during the solubilisation procedure of the foaming agent (or of the mixture of foaming agents), thus producing a multi-layer material with three, four, five or even more layers having a different morphology and/or density. Preferably, in accordance with the first object of the present invention, the pressure is released instantaneously at a speed of no less than 10 bars/s, more preferably no less than 100 bars/s.

A second object of the present invention is represented by a foamed polymeric material with a multi-layer structure obtained by the process according to the first object of the present invention.

Advantageously, in accordance with the second object of the present invention, said foamed polymeric material comprises at least two layers having different density and/or morphology without having discontinuities in morphology and/or density at the interface between said at least two layers. Preferably, said foamed polymeric material comprises at least two layers having different density and/or morphology and has a gradual variation in the density and/or morphology present in the foamed material.

In accordance with the second object of the present invention, the foamed polymeric material preferably consists of multi-layer pre-foamed beads or multi-layer foamed sheets.

Advantageously, said multi-layer foamed sheets comprise at least one layer with lower density and finer morphology and at least one layer with higher density and coarser morphology.

Advantageously, said multi-layer foamed sheets comprise at least one layer with lower density and coarser morphology and at least one layer with higher density and finer morphology.

Advantageously, said multi-layer foamed sheets comprise at least one layer with lower density and at least one layer with higher density, with uniform morphology.

Advantageously, said multi-layer foamed sheets comprise at least one layer with coarser morphology and at least one layer with finer morphology, with uniform density.

Advantageously, said multi-layer pre-foamed beads comprise at least one non-foamed layer and at least one pre-foamed layer, where said non-foamed layer is in a radially external position with respect to the pre-foamed layer.

With the process of the present invention it is therefore for the first time possible to obtain a foamed polymeric material with a multi-layer structure lacking discontinuities, typical of the materials obtained by bonding or welding separately obtained layers together, and with a uniform composition, thus avoiding the use of composite materials.

A third object of the present invention is therefore represented by a foamed polymeric material with a multi-layer structure and uniform composition, where said multi-layer structure comprises at least two layers and where each of said at least two layers has a specific and different morphology and/or density, characterised in that it presents a gradual variation in density and/or morphology at the interface between said at least two layers present in the foamed material.

In particular, the foamed polymeric material, in accordance with the third object of the present invention, is characterised in that it does not present discontinuities in morphology and density at the interface between said at least two layers.

Advantageously, in accordance with the second and third objects of the present invention, said foamed polymeric material comprises at least two layers having different density and/or morphology and having a gradual variation in the density and/or morphology present in the foamed material.

In particular, the multi-layer structure comprises at least three layers, and more particularly comprises three, four, five or more layers with specific and different morphology and/or density.

Figure 2A:
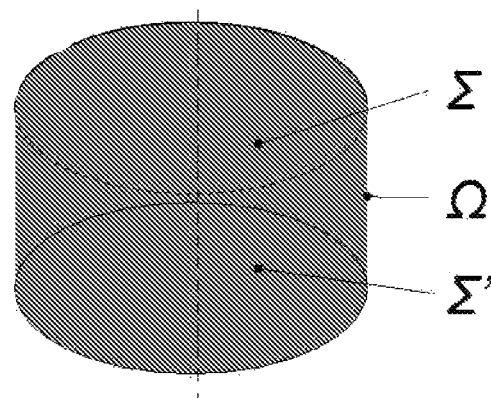
FIG. 2A shows a diagram of the sample used in examples 1-6, with the base surfaces Σ eΣ' and the side surface Ω highlighted.
Figure 2B:
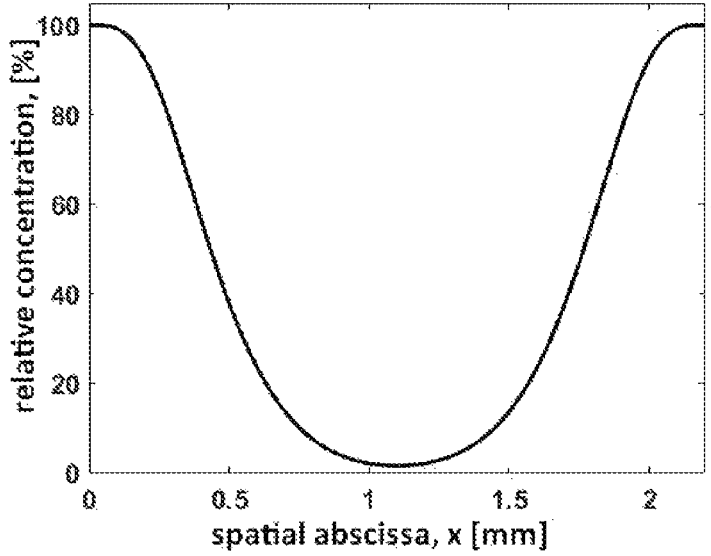
FIG. 2B shows the axial concentration profile of the foaming agent along the entire axial profile of the sample, immediately prior to the release of pressure to allow the foaming used in example 1.
Figure 2C:
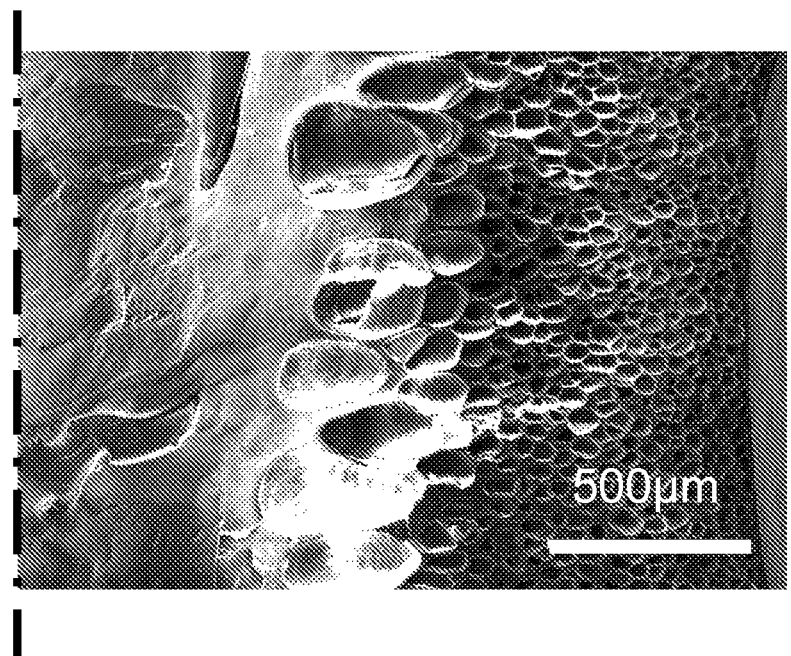
FIG. 2C shows a scanning electron microscope photograph of the foam section resulting from the sample subjected to the procedure of example 1 (scale bar equal to 500 μm). For clarity, only half of the sample is shown, symmetrical with respect to the vertical line indicated in the figure.
Figure 3A:
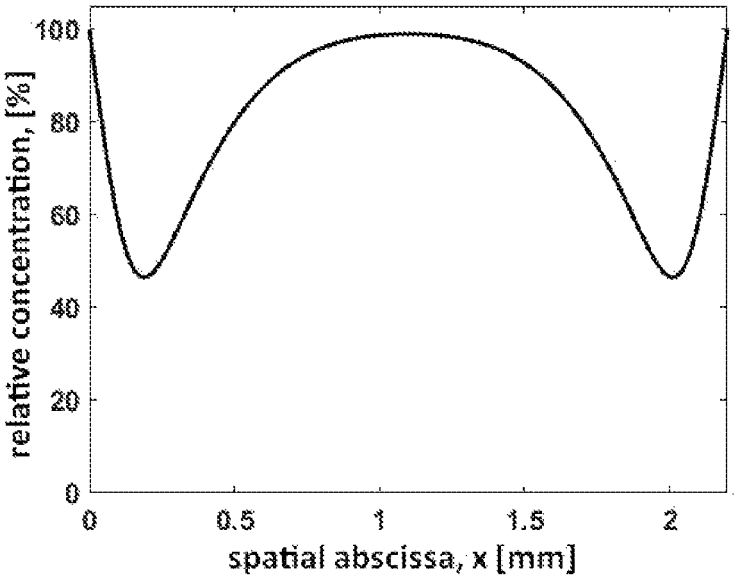
FIG. 3A shows the axial concentration profile of the foaming agent immediately prior to the release of pressure to allow the foaming used in example 2.
Figure 3B:
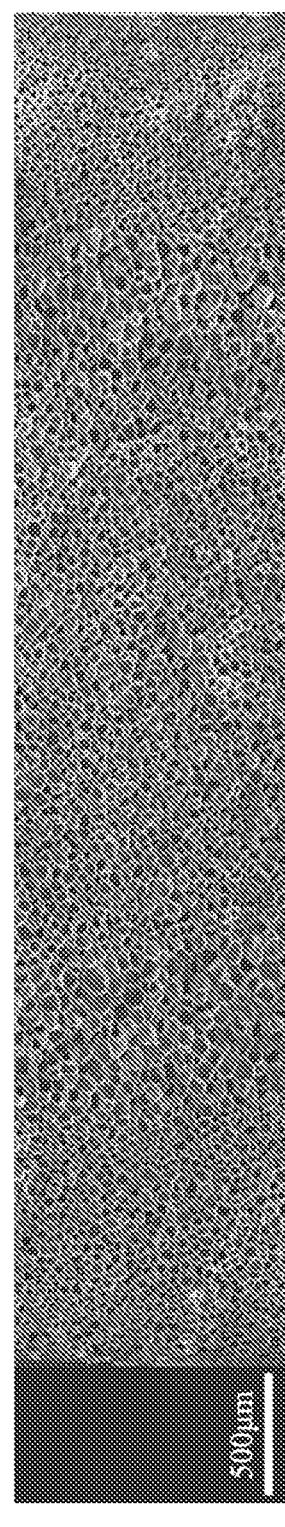
FIG. 3B shows a scanning electron microscope photograph of the foam section resulting from the sample subjected to the procedure of example 2 (scale bar equal to 500 μm). An entire section of the sample is shown to highlight the 5 symmetrical layers.
Figure 11A:
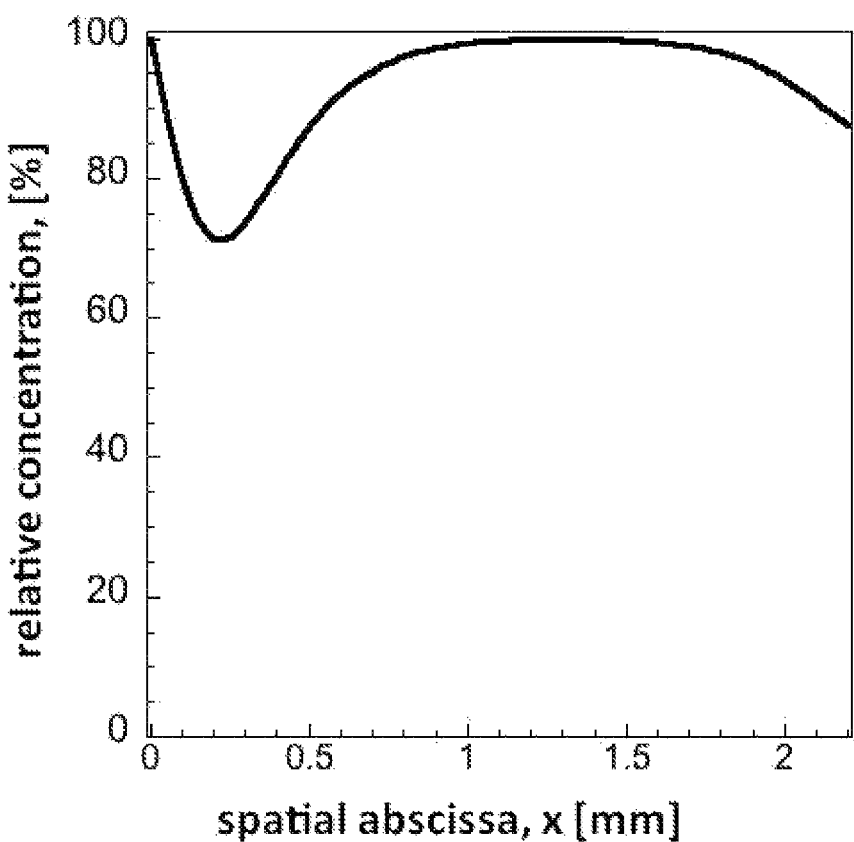
FIG. 11A shows the axial concentration profile of the foaming agent along the entire axial profile of the sample, immediately prior to the release of pressure to allow the foaming used in example 10.
Figure 11B:
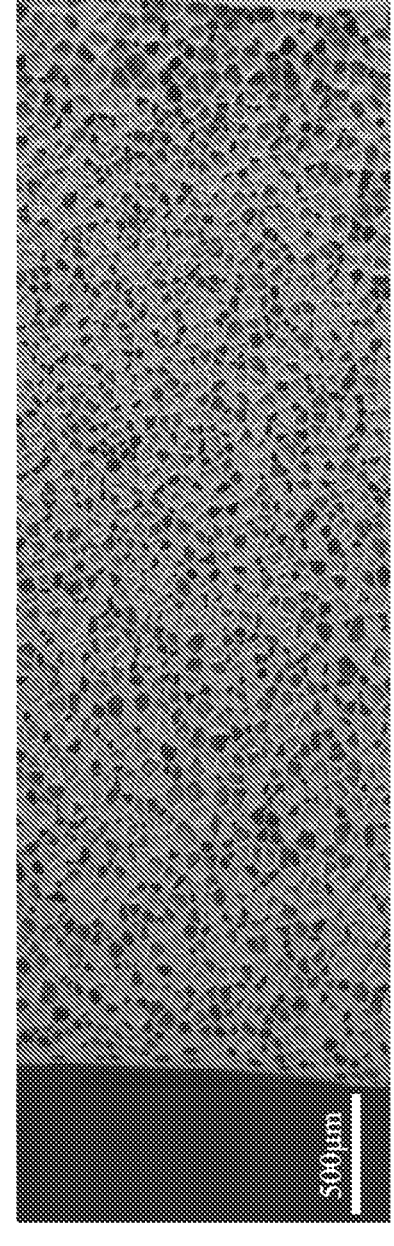
FIG. 11B shows a scanning electron microscope photograph of the foam section resulting from the sample subjected to the procedure of example 10 (scale bar equal to 500 μm). An entire section of the sample is shown to highlight the 4 non-symmetrical layers.

The three-layer materials are particularly preferred, the embodiment of which is described in examples 1, 4, 5, and 6, and illustrated in FIGS. 2C, 5B, 6B, and 7B, as well as the five-layer materials, the embodiment of which is described in examples 2 and 10, and illustrated in FIGS. 3B and 11B.

The polymeric material according to the second and third objects of the present invention lends itself to being used for the creation of manufactured products of complex shape with multi-gradient and anisotropic morphology, that is to say with a morphology determined by the porosity.

A fourth object of the present invention is represented by a manufactured product made wholly or in part with a foamed polymeric material with a multi-layer structure and uniform composition, where said multi-layer structure comprises at least two layers and where each of said at least two layers has a specific and different morphology and/or density, characterised in that it presents a gradual variation in density and/or morphology at the interface between said at least two layers present in the foamed material.

Preferably, in accordance with the fourth object of the present invention, said multi-layer structure comprises a multi-gradient morphology.

Advantageously, in accordance with the fourth object of the present invention, said multi-layer structure comprises an anisotropic morphology.

In particular, in accordance with the fourth object of the present invention, said manufactured product is represented, for example, by protection systems (shin guards, back braces, shoulder and elbow pads, knee pads, shells and pads, bullet-proof vests), helmets and helms, orthopaedic prostheses, dental prostheses, epidermis prostheses, tissue engineering scaffolds, absorption and soundproofing slabs and systems, thermal insulation systems and slabs, soles and elements for sports shoes, panels for cars, sports equipment, furnishings, packaging, filtration membranes and systems, sacrificial foams for ceramic materials and porous metals, foams for diffusers and aerators, biomedical systems, pads and patches for controlled drug delivery, progressive mechanical response systems, progressive functional response systems, electromagnetic shielding systems, catalytic systems, foams for aeronautics and aerospace, foams for optoelectronics, flotation systems, frames and chassis, and glasses frames.

In particular, in accordance with the fourth object of the present invention, said manufactured product is represented, for example, by orthopaedic prostheses, i.e. medical devices capable of replicating the bone structure of a skeletal segment of a human or animal body with the same structural characteristics.

In particular, the orthopaedic prosthesis according to the fourth object of the present invention comprises orthopaedic endoprostheses of the lower limbs (foot, ankle, knee, femur, hip), of the upper limbs (hand, wrist, elbow, humerus, shoulder), and of the vertebral column.

The present invention will now be illustrated with reference to materials and methods described for explanatory, but not limiting, purposes in the following experimental part.

Experimental Part

Figure 1B:
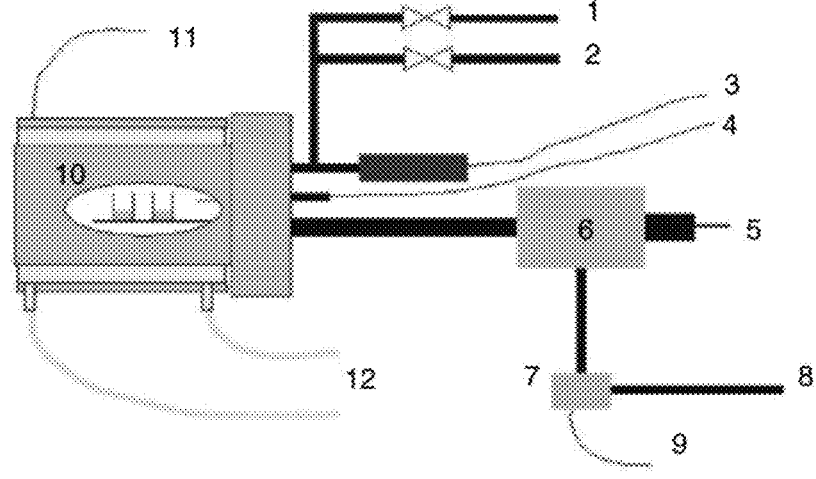
FIG. 1B shows a diagram of the discontinuous foaming apparatus used in the present invention.

For the preparation of the foam samples, the batch foaming system illustrated in FIG. 1 was used, of which some details are given below. FIG. 1 shows a photograph (FIG. 1A) and a diagram (FIG. 1B) of the discontinuous foaming apparatus used in the present invention.

The reactor is cylindrical, thermoregulated and pressurised, with a volume of 0.3 L (HiP, model BC-1). The reactor was modified to allow the measurement and control of the process parameters of interest.

For temperature control, an electric heater (11) was used as a heating element and a heat exchanger with an oil bath (12) as a cooling element.

The heater (11) and the exchanger (12) were controlled by a PID thermoregulator (Ascon, model X1), which read the temperature inside the reactor using a Pt100 probe (4).

A Schaevitz pressure transducer, model P943 (3), was used to measure pressures during the saturation step and to record the pressure pattern during the release of the foaming agent. The valve (1) was connected to the expanding gas supply while the valve (2) was connected to a vacuum pump.

The pressure release system consists of an HiP ball discharge valve, model 15-71 NFB (5), an HiP electromechanical actuator, model 15-72 NFB TSR8 (6), and a solenoid valve (7) connected to the piping for the compressed air (8) and the cable (9) for the solenoid valve actuation signal (7). This system allowed the opening of the valve to be reproduced. The pressure pattern over time during pressure release, P (t), was recorded using a DAQ PCI6036E data acquisition system, National Instruments, Austin, TX, USA.

The pressure program was managed by the Teledyne ISCO 500D volumetric pump (Lincoln NE, USA). Through the serial interface of the pump controller it was possible to control the pump via a computer and implement any pressure program. In addition, the controller can handle up to four pumps for different fluids.

The creation of a variable condition of the solubilisation step can occur through a variation of the solubilisation pressure of the foaming agent, with a periodic pattern (for example, a triangular or sinusoidal wave), or with a non-periodic pattern (for example, a linear or curvilinear profile), as described in the following examples.

Example 1—Invention

In this example, the polymer used is a polystyrene (PS), code N2380, supplied by Versalis SpA (Mantua, Italy) with a mean molecular weight, density and melt flow index respectively equal to 300 kDa, 1.05 g/cm$^3$ and 2.0 g/10 min at 200° C. and 10 kg, respectively.

The sample consists of a cylindrical disk of PS with a diameter of 25 mm and thickness of 2.2 mm. Protecting its side surface ($\Omega$ in FIG. 2A) with a metal barrier film (perfectly impermeable to foaming agents), the only surfaces exposed to contact with the foaming agent are the two upper and lower bases ($\Sigma$ and $\Sigma'$ in FIG. 2A). In this way mass transport occurs in the direction of the cylinder axis and can be studied as a one-dimensional problem. The use of the barrier film is, in this case and in those described in examples 2, 3, 4, 5 and 6, in which the sample to be foamed is cylindrical, dictated solely by the need to render the one-dimensional treatment of the material transport more rigorous. It is not considered necessary for the purpose of obtaining the multi-layer structure.

The sample was housed in the batch foaming system illustrated in FIG. 1 and described above, at room temperature. The reactor was then closed and brought to a temperature of 100° C.

The system was then subjected to the solubilisation step of the expanding $CO_2$ gas using the pressure profile described in Table 1.

TABLE 1

| | Initial pressure (bars) | Final pressure (bars) | Duration (minutes) |
|---|---|---|---|
| Step 1 | 0 | 150 | 0.2 |
| Step 2 | 150 | 200 | 2.6 |
| Step 3 | 200 | 100 | 5.2 |

As shown in Table 1, the pressure profile comprised three phases:

in step 1, the pressure of the expanding $CO_2$ gas was brought from atmospheric pressure to 150 bars with a linear ramp in 0.2 minutes (12 seconds);

in step 2, the pressure of the expanding $CO_2$ gas was increased from 150 to 200 bars with a linear ramp in 2.6 minutes (156 seconds);

in step 3, the pressure of the expanding $CO_2$ gas was decreased from 200 to 100 bars with a linear ramp in 5.2 minutes (312 seconds).

At the end of step 3 the pressure was instantaneously released (at a maximum speed of 1000 bars/s) for foaming.

Immediately before the release of pressure, at the end of step 3, the concentration profile, as calculated using Comsol Multiphysics 10.0 simulation software, using data on $CO_2$ diffusivity in PS at 100° C. reported by Sato et al., in "Solubilities and diffusion coefficients of carbon dioxide in poly(vinyl acetate) and polystyrene", The Journal of Supercritical Fluids 19 (2001) 187-198, and the geometry described above resulted in that shown in FIG. 2B.

In particular, three different foamed areas were recognised and distinguished in the foamed cylindrical disk, two near the base surfaces, with a high concentration of foaming agent, and a central area with a low concentration of foaming agent.

From this concentration profile, upon the release of pressure, the different foaming capacities of the different areas were found.

The areas with a high concentration of foaming agent were foamed with a morphology and density depending on the foaming conditions (here in particular the temperature of 100° C., the concentration of about 6% by weight and the pressure release rate of 1000 bars/s), while the central area lacking foaming agent was not foamed, even though it had the same operating conditions as the high concentration areas.

In particular, FIG. 2C shows a scanned electron microscope image of the section of the produced foam, with an evident three-layer structure. The two areas near the base surfaces were foamed, with a density of about 0.1 g/cm$^3$, and minimum pore size of about 20 μm, while the central area was not foamed.

Through the use of a gradual variation in the concentration profile, a clear separation between the three areas was not created. On the contrary, a gradual variation of both density and morphology was detected. In particular, the lessening concentration of the foaming agent towards the centre of the disc led to an increase in the size of the bubbles (from about 20 μm to about 300 μm) and an increase in density from 0.1 to 1 g/cm$^3$.

Using specific solubilisation programs, it is possible to design the number, thicknesses, morphologies and densities of the different layers, as described in the following examples.

Example 2—Invention

An analogous sample of PS, for composition, geometry and positioning of the barrier film, to that described in Example 1, was housed in the reactor of the batch foaming apparatus illustrated in FIG. 1 and previously described at room temperature. The reactor was then closed and brought to a temperature of 100° C.

The system was then subjected to the solubilisation step of the expanding $CO_2$ gas using the pressure profile described in Table 2.

TABLE 2

| | Initial pressure (bars) | Final pressure (bars) | Duration (minutes) |
|---|---|---|---|
| Step 1 | 0 | 130 | 0.2 |
| Step 2 | 130 | 130 | 120 |

TABLE 2-continued

|  | Initial pressure (bars) | Final pressure (bars) | Duration (minutes) |
|---|---|---|---|
| Step 3 | 130 | 80 | 9.6 |
| Step 4 | 80 | 130 | 15.6 |

As shown in Table 2, the pressure profile comprised four phases:

in step 1, the pressure of the expanding $CO_2$ gas was brought from atmospheric pressure to 130 bars with a linear ramp in 0.2 minutes (12 seconds);

in step 2, the pressure was maintained at 130 bars for 120 minutes;

in step 3, the pressure of the expanding $CO_2$ gas was decreased from 130 to 80 bars with a linear ramp in 9.6 minutes (576 seconds);

in step 4, the pressure of the expanding $CO_2$ gas was increased from 80 to 130 bars with a linear ramp in 15.6 minutes (936 seconds).

At the end of step 4 the pressure was instantaneously released (at a maximum speed of 1000 bars/s) for foaming.

Immediately before the release of pressure, at the end of step 4, the concentration profile, as calculated using Comsol Multiphysics 10.0 simulation software, using data on $CO_2$ diffusivity in PS at 100° C. reported by Sato et al., in "Solubilities and diffusion coefficients of carbon dioxide in poly(vinyl acetate) and polystyrene", The Journal of Supercritical Fluids 19 (2001) 187-198, and the geometry described above resulted in that shown in FIG. 3A.

In particular, five different foamed areas were recognised and distinguished in the foamed cylindrical disk, two near the base surfaces, with a high concentration of foaming agent, two intermediate areas with a lesser concentration, and a central area with again a high concentration of foaming agent.

From this concentration profile, upon the release of pressure, the different foaming capacities of the different areas were found.

The areas with a high concentration of foaming agent (the two near the surface and the central one) were foamed (indicated in FIG. 3B with "highly foamed area") with a morphology and density depending on the foaming conditions (here in particular the temperature of 100° C., the concentration of about 5% by weight and the pressure release rate of 1000 bars/s), while the two intermediate areas with less foaming agent (concentration of about 3%), had a lower degree of foaming (shown in FIG. 3B with "less foamed area").

Figure 3C:
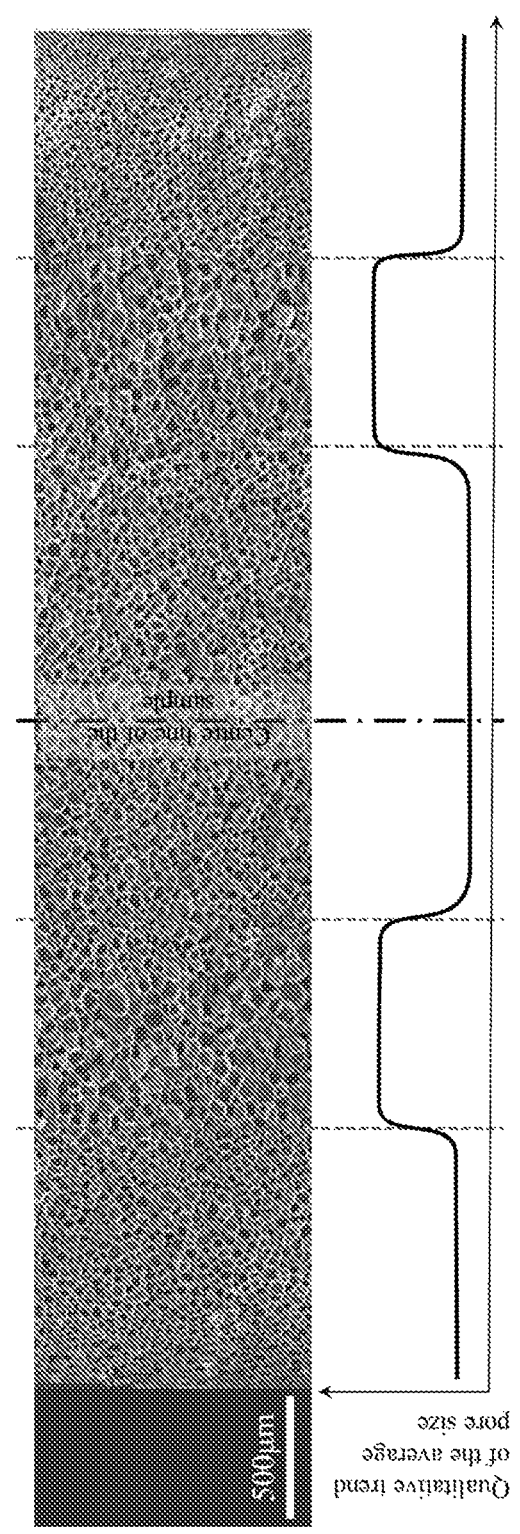
FIG. 3C shows the same image shown in FIG. 3B, with a superimposed graph showing the qualitative trend of the pore size.

In particular, FIGS. 3B-D show some images of the section of foam produced at different magnifications taken with a scanning electron microscope, with a clear five-layer structure. The two areas near the base surfaces and the central area were foamed, with a density of about 0.1 g/cm³, and pore size of about 20 μm. The two intermediate areas were less foamed, with a density of 0.3 g/cm³ and pore size of about 80 μm.

Also in this example, through the use of a gradual variation of the observed concentration profile, a clear separation between the different areas was not created. On the contrary, a gradual variation of both density and morphology was detected. Images 3C and 3D show some enlargements of the transition zones, where the variation in the size of the bubbles can be noted.

The process of the present invention allows broad freedom in design, differently from the method described in Zhou C. et al., in "Fabrication of functionally graded porous polymer via supercritical $CO_2$ foaming", Composites: Part B 42 (2011) 318-325.

Furthermore, in the foamed sample it was observed, as can be seen in FIGS. 2C and 3B, that no discontinuity in morphologies was formed, differently from the products layered by coupling present in the products obtained with the methods known in the art.

Example 3—Comparison

An analogous sample of PS, for composition, geometry and positioning of the barrier film, to that described in Example 1, was housed in the reactor of the batch foaming apparatus illustrated in FIG. 1 and previously described at room temperature. The reactor was then closed and brought to a temperature of 100° C.

The system was then subjected to the solubilisation step of the expanding $CO_2$ gas using the pressure profile described in Table 3.

TABLE 3

|  | Initial pressure (bars) | Final pressure (bars) | Duration (minutes) |
|---|---|---|---|
| Step 1 | 0 | 100 | 0.2 |
| Step 2 | 100 | 100 | 180 |

As shown in Table 3, the pressure profile comprised two steps:

in step 1, the pressure of the expanding $CO_2$ gas was brought from atmospheric pressure to 100 bars with a linear ramp in 0.2 minutes (12 seconds);

in step 2, the expanding $CO_2$ gas pressure was kept at 100 bars for 180 minutes to allow the complete solubilisation of the foaming agent.

At the end of step 2 the pressure was instantaneously released (at a maximum speed of 1000 bars/s) for foaming.

Immediately before the release of pressure, at the end of step 2 the concentration profile is constant and equal to about 6% by weight of $CO_2$.

From this concentration profile, there was uniform foaming with the release of pressure, both in terms of density (about 0.1 g/cm³) and in terms of morphology (average bubble size of 50 μm).

This type of uniform structure is typical of the state of the art.

Figure 4A:
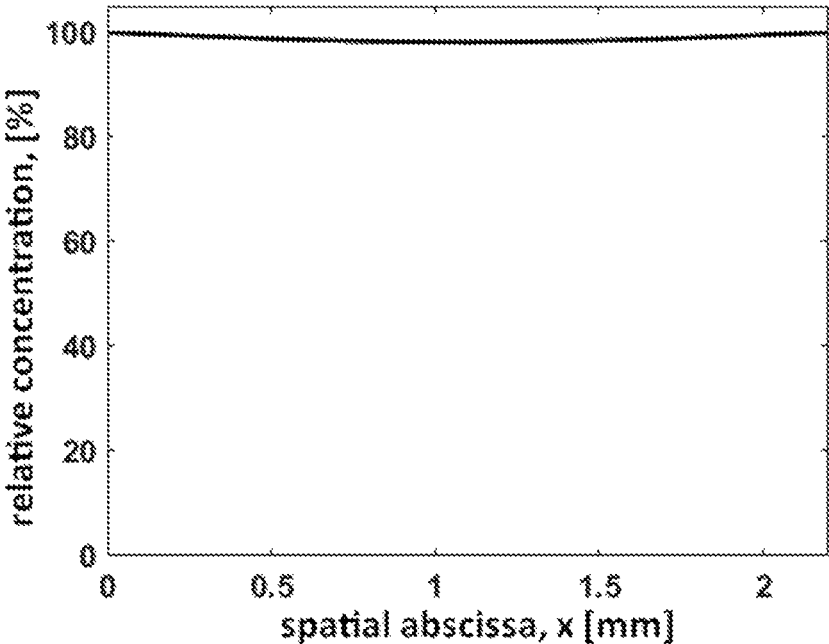
FIG. 4A shows the axial concentration profile of the foaming agent along the entire axial profile of the sample, immediately prior to the release of pressure to allow the foaming used in example 3.
Figure 4B:
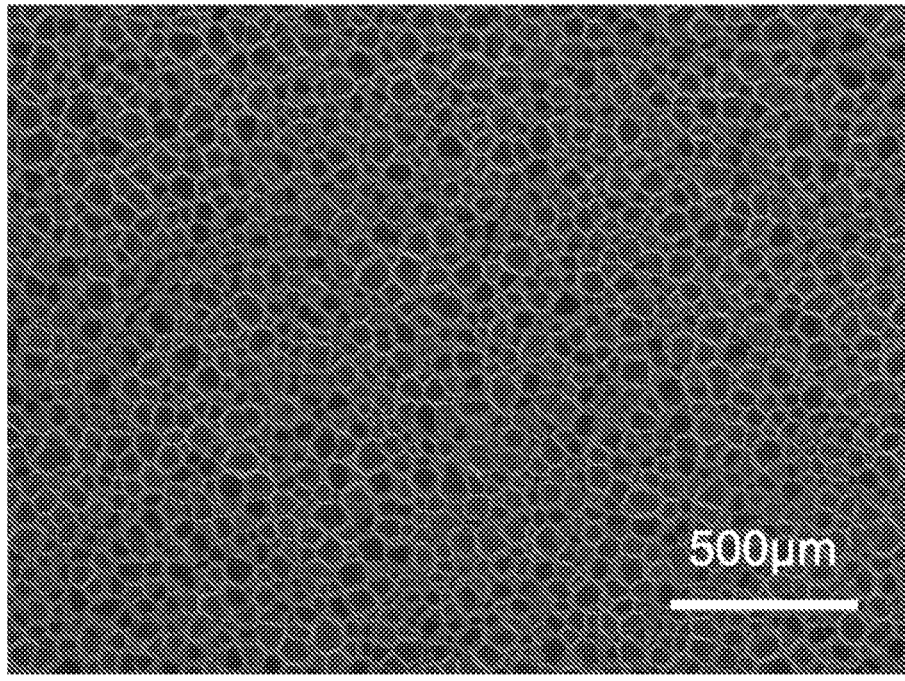
FIG. 4B shows a scanning electron microscope photograph of the foam section resulting from the sample subjected to the procedure of example 3 (scale bar equal to 500 μm).

A graph showing the concentration values of $CO_2$ at the end of phase 2 (immediately before foaming), expressed as a percentage with respect to the equilibrium concentration at maximum pressure, as a function of the spatial abscissa "cylinder axis", x, is shown in FIG. 4A. A scanned electron microscope image of the resulting foam is shown in FIG. 4B.

Example 4—Comparison

An analogous sample of PS, for composition, geometry and positioning of the barrier film, to that described in Example 1, was housed in the reactor of the batch foaming apparatus illustrated in FIG. 1 and previously described at room temperature. The reactor was then closed and brought to a temperature of 100° C.

The system was then subjected to the solubilisation step of the expanding $CO_2$ gas using the pressure profile described in Table 4.

15

TABLE 4

|  | Initial pressure (bars) | Final pressure (bars) | Duration (minutes) |
| --- | --- | --- | --- |
| Step 1 | 0 | 100 | 0.2 |
| Step 2 | 100 | 100 | 20 |

As shown in Table 4, the pressure profile comprised two steps:

in step 1, the pressure of the expanding $CO_2$ gas was brought from atmospheric pressure to 100 bars with a linear ramp in 0.2 minutes (12 seconds);

in step 2, the pressure was maintained at 100 bars for 20 minutes;

At the end of step 2 the pressure was instantaneously released (at a maximum speed of 1000 bars/s) for foaming.

Immediately prior to the release of pressure, at the end of step 2, the concentration profile is that described by the error function (erf), widely described in scientific and technical literature.

In particular, the concentration of foaming agent in the cylindrical disk progressively changes from the outside to the inside, as described in Zhou C. et al., in "Fabrication of functionally graded porous polymer via supercritical $CO_2$ foaming", Composites: Part B 42 (2011) 318-325. In the outer layer, near the external surface the gas concentration is 6% by weight, while in the inner layer it is null, as the solubilisation time (20 minutes in this case) is much lower than that necessary for complete solubilisation.

Figure 5A:
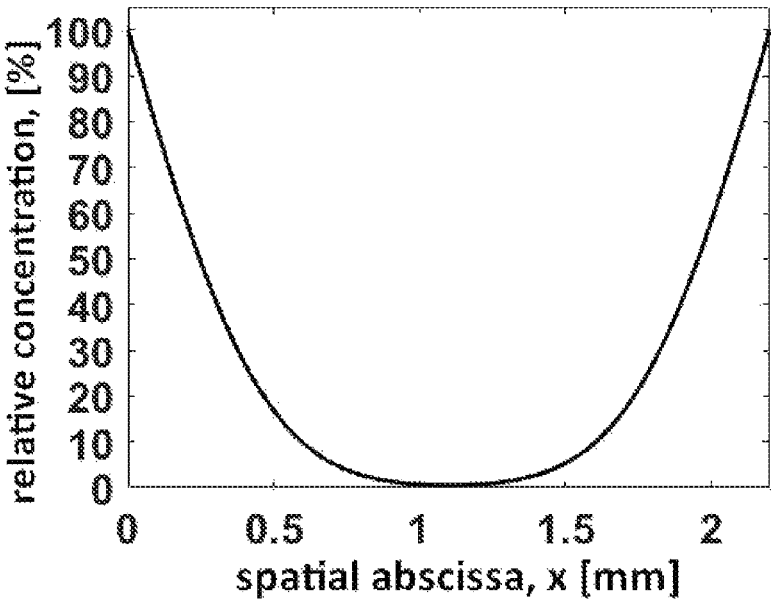
FIG. 5A shows the axial concentration profile of the foaming agent along the entire axial profile of the sample, immediately prior to the release of pressure to allow the foaming used in example 4.
Figure 5B:
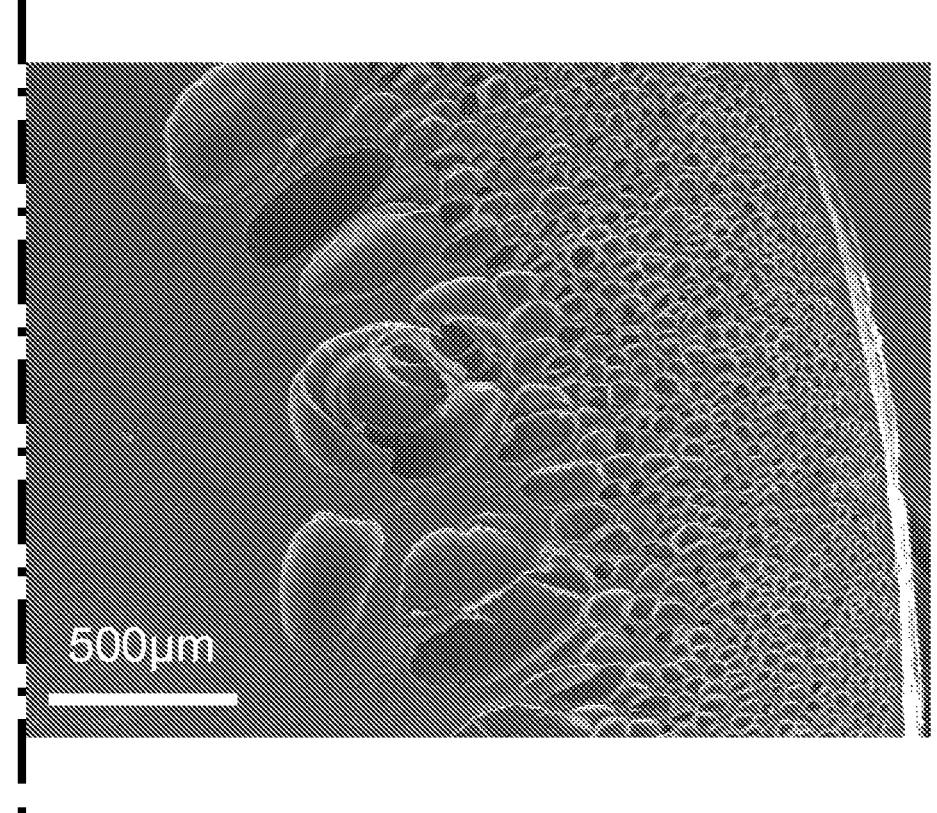
FIG. 5B shows a scanning electron microscope photograph of the foam section resulting from the sample subjected to the procedure of example 4 (scale bar equal to 500 μm). For clarity, only half of the sample is shown, symmetrical with respect to the vertical line indicated in the figure.

A graph showing the concentration values of $CO_2$ at the end of phase 2 (immediately before foaming), expressed as a percentage with respect to the equilibrium concentration at maximum pressure, as a function of the spatial abscissa "cylinder axis", x, is shown in FIG. 5A. A scanned electron microscope image of the resulting foam is shown in FIG. 5B.

In this foam three different foaming areas can be recognised and distinguished, two near the base surfaces, foamed with a density of about 0.1 $g/cm^3$ and fine morphology, and a non-foamed central area. In particular, the foamed area has a non-uniform morphology, with the number of bubbles per unit of volume decreasing gradually from the outer surface towards the inner one (and, correspondingly, a larger bubble size), indicating the lower concentration of gas from the outside inward. This type of structure, known in the state of the art (Zhou C. et al., in "Fabrication of functionally graded porous polymer via supercritical $CO_2$ foaming", Composites: Part B 42 (2011) 318-325), derives from the "error function" solution to the problem of mass transport of the foaming agent, at constant external pressure. As such, there is no possibility of modulating the structure, for example to modify the thicknesses of the foamed/non-foamed layers and/or the width of the gradient area. Moreover, a fortiori, it is impossible to have non-monotonic patterns in the thickness concentration, if not those dictated by reasons of symmetry with respect to the external surfaces exposed to the atmosphere of the foaming agent.

Example 5—Invention

An analogous sample of PS, for composition, geometry and positioning of the barrier film, to that described in Example 1, was housed in the reactor of the batch foaming apparatus illustrated in FIG. 1 and previously described at room temperature. The reactor was then closed and brought to a temperature of 100° C.

The system was then subjected to the solubilisation step of the expanding $CO_2$ gas using the pressure profile described in Table 5.

TABLE 5

|  | Initial pressure (bars) | Final pressure (bars) | Duration (minutes) |
| --- | --- | --- | --- |
| Step 1 | 0 | 200 | 0.2 |
| Step 2 | 200 | 200 | 9.6 |
| Step 3 | 200 | 100 | 0.2 |
| Step 4 | 100 | 100 | 5 |

As shown in Table 5, the pressure profile comprised four phases:

in step 1, the pressure of the expanding $CO_2$ gas was brought from atmospheric pressure to 200 bars with a linear ramp in 0.2 minutes (12 seconds);

in step 2, the expanding $CO_2$ gas pressure was kept at 200 bars for 9.6 minutes;

in step 3, the pressure of the expanding $CO_2$ gas was decreased from 200 to 100 bars in 0.2 minutes (12 seconds);

in step 4, the expanding $CO_2$ gas pressure was kept at 100 bars for 5 minutes;

At the end of step 4 the pressure was instantaneously released (at a maximum speed of 1000 bars/s) for foaming.

Immediately before the release of pressure, at the end of step 4, the concentration profile, as calculated using Comsol Multiphysics 10.0 simulation software, using data on $CO_2$ diffusivity in PS at 100° C. reported by Sato et al., in "Solubilities and diffusion coefficients of carbon dioxide in poly(vinyl acetate) and polystyrene", The Journal of Super-critical Fluids 19 (2001) 187-198, and the geometry described above resulted in that shown in FIG. 6A.

In particular, three different foamed areas were recognised and distinguished in the foamed cylindrical disk, two near the base surfaces, with a high concentration of foaming agent, and a central area with a low concentration of foaming agent. Unlike the concentration profile shown in FIG. 5A, in this case the profile is initially flat in the areas of high concentration, then decreasing inwards. In the case of FIG. 5A, on the other hand, no area with a constant concentration of gas was obtained.

From this concentration profile, upon the release of pressure, the different foaming capacities of the different areas were found.

The areas with a high concentration of foaming agent were foamed with a morphology and density depending on the foaming conditions, while the central area lacking foaming agent was not foamed, even though it had the same operating conditions as the high concentration areas.

Figures 6A, 6B:
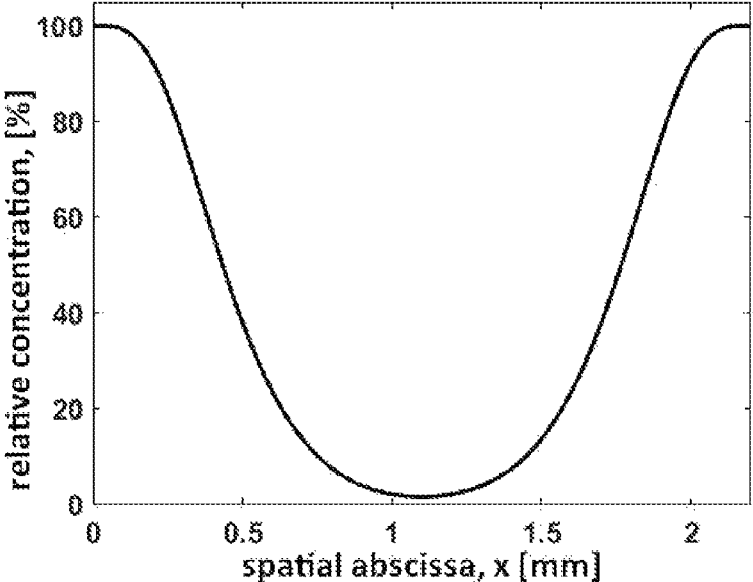
FIG. 6A shows the axial concentration profile of the foaming agent immediately prior to the release of pressure to allow the foaming used in example 5.
FIG. 6B shows a scanning electron microscope photograph of the foam section resulting from the sample subjected to the procedure of example 5 (scale bar equal to 500 μm). For clarity, only half of the sample is shown, symmetrical with respect to the vertical line indicated in the figure.

In particular, FIG. 6B shows a scanned electron microscope image of the section of the produced foam, with an evident three-layer structure. The two areas near the base surfaces were foamed, with a density of about 0.1 $g/cm^3$, and minimum pore size of about 20 μm, while the central area was not foamed. Differently from the case described in FIG. 5B, however, in this case the foamed morphology is more uniform, as a consequence of the outermost area with a constant concentration, and only further inside does the number of bubbles decrease (and the average size increases) as a consequence of the lower concentration of gas.

Example 6—Invention

An analogous sample of PS, for composition, geometry and positioning of the barrier film, to that described in Example 1, was housed in the reactor of the batch foaming apparatus illustrated in FIG. 1 and previously described at room temperature. The reactor was then closed and brought to a temperature of 100° C.

The system was then subjected to the solubilisation step of the expanding $CO_2$ and 134a (1,1,1,2-tetrafluoroethane) gas using the pressure profile described in Table 6.

TABLE 6

|  | Initial pressure (bars) | Final pressure (bars) | Duration (minutes) |
|---|---|---|---|
| Step 1 | 0 | 100 ($CO_2$) | 0.2 |
| Step 2 | 100 ($CO_2$) | 100 ($CO_2$) | 9.6 |
| Step 3 | 100 ($CO_2$) | 100 (134a) | 0.2 |
| Step 4 | 100 (134a) | 100 (134a) | 2 |

As shown in Table 6, the pressure profile comprised four phases:

- in step 1, the pressure of the expanding $CO_2$ gas was brought from atmospheric pressure to 100 bars with a linear ramp in 0.2 minutes (12 seconds);
- in step 2, the expanding $CO_2$ gas pressure was kept at 100 bars for 9.6 minutes;
- in step 3, the pressure of the expanding $CO_2$ gas was decreased from 100 to 0 bars in 0.2 minutes (12 seconds); at the same time, in the same step, the external pressure was equilibrated, while still maintaining the total external pressure equal to 100 bars, using a second 134a gas of higher molecular weight;
- in step 4, the 134a gas pressure was kept at 100 bars for 2 minutes;

At the end of step 4 the pressure was instantaneously released (at a maximum speed of 1000 bars/s) for foaming.

Figure 7A:
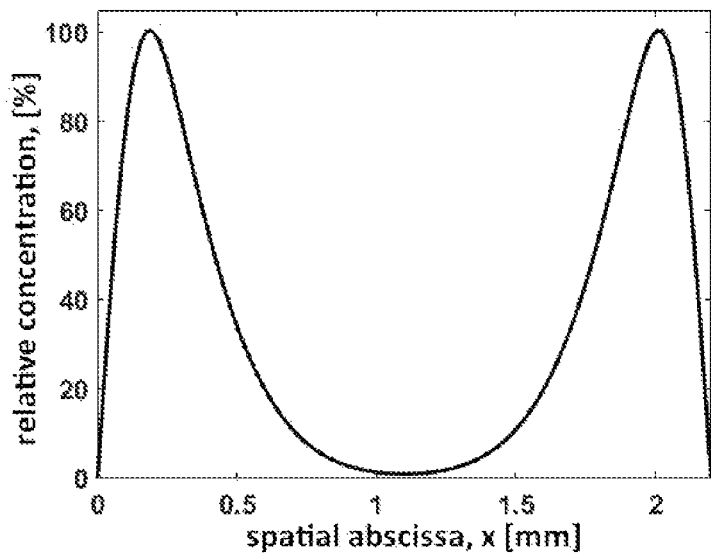
FIG. 7A shows the axial concentration profile of the foaming agent immediately prior to the release of pressure to allow the foaming used in example 6.

Immediately before the release of pressure, at the end of step 4, the concentration profile, as calculated using Comsol Multiphysics 10.0 simulation software, using data on $CO_2$ diffusivity in PS at 100° C. reported by Sato et al., in "Solubilities and diffusion coefficients of carbon dioxide in poly(vinyl acetate) and polystyrene", The Journal of Supercritical Fluids 19 (2001) 187-198, and the geometry described above resulted in that shown in FIG. 7A. To use this calculation, the diffusion coefficient of the gas 134a was set much higher than that of the $CO_2$, neglecting, for all practical effects, the absorption of 134a in the polymer.

In particular, three different foamed areas were recognised and distinguished in the foamed cylindrical disk, two near the base surfaces, with a high concentration of foaming agent, and a central area with a low (near zero) concentration of foaming agent. Differently from the concentration profile shown in FIG. 5A, in this case the concentration of $CO_2$ is low near the surface.

From this concentration profile, upon the release of pressure, the different foaming capacities of the different areas were found.

The areas with a high concentration of foaming agent were foamed with a morphology and density depending on the foaming conditions, while the central area lacking foaming agent was not foamed.

Figure 7B:
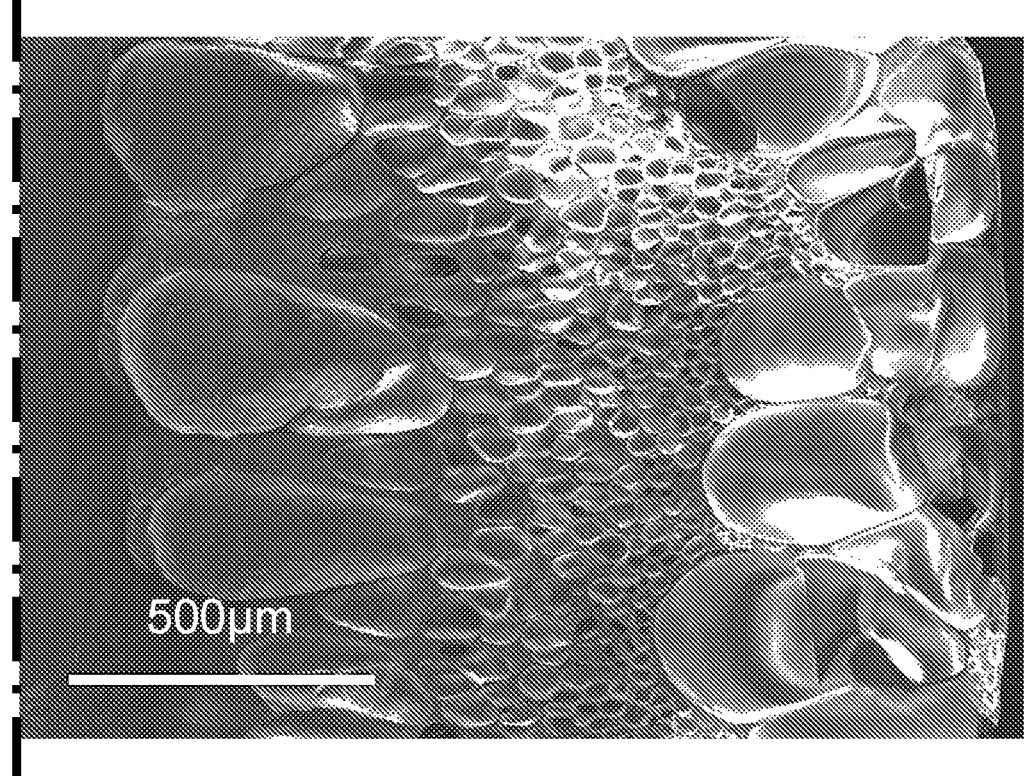
FIG. 7B shows a scanning electron microscope photograph of the foam section resulting from the sample subjected to the procedure of example 6 (scale bar equal to 500 μm). For clarity, only half of the sample is shown, symmetrical with respect to the vertical line indicated in the figure.

In particular, FIG. 7B shows a scanned electron microscope image of the section of the produced foam, with an evident three-layer structure. The two areas near the base surfaces were foamed, but the central area was not foamed. Differently from the case described in FIG. 5B, however, in this case the foamed morphology can be described by two gradients, with a density of bubbles, moving from the outside towards the inside, first increasing and then decreasing, corresponding to the pressure profile shown in FIG. 7A.

Example 7—Comparison

In this example, the polymer used is a polystyrene (PS), code N2380, supplied by Versalis SpA (Mantua, Italy) with a mean molecular weight, density and melt flow index respectively equal to 300 kDa, 1.05 $g/cm^3$ and 2.0 g/10 min at 200° C. and 10 kg, respectively.

The sample consists of a sphere of PS with a diameter of 1 mm, schematically shown in FIG. 8. These objects are used to make the so-called pre-foamed beads to be sintered in systems using water vapours to create a finished product downstream of a sintering process of the pre-foamed beads. In this system, mass transport occurs in the radial direction and can be studied as a one-dimensional problem.

The sample devoid of any barrier layer was housed in the batch foaming system illustrated in FIG. 1 and described above, at room temperature. The reactor was then closed and brought to a temperature of 100° C.

The system was then subjected to the solubilisation step of the expanding $CO_2$ gas using the pressure profile described in Table 7.

TABLE 7

|  | Initial pressure (bars) | Final pressure (bars) | Duration (minutes) |
|---|---|---|---|
| Step 1 | 0 | 100 | 0.2 |
| Step 2 | 100 | 100 | 10 |

As shown in Table 7, the pressure profile comprised two steps:

- in step 1, the pressure of the expanding $CO_2$ gas was brought from atmospheric pressure to 100 bars with a linear ramp in 0.2 minutes (12 seconds);
- in step 2, the expanding $CO_2$ gas pressure was kept at 100 bars for 10 minutes to allow the complete solubilisation of the foaming agent.

At the end of step 2 the pressure was instantaneously released (at a maximum speed of 1000 bars/s) for foaming.

Immediately before the release of pressure, at the end of step 2 the concentration profile is constant and equal to about 6% by weight of $CO_2$. The gas concentration profile is shown in FIG. 8A.

From this concentration profile, there was uniform foaming with the release of pressure, both in terms of density (about 0.1 $g/cm^3$) and in terms of morphology (average bubble size of 50 μm).

This type of uniform structure is typical of the state of the art.

A scanned electron microscope image of the resulting foam is shown in FIG. 8B.

Example 8—Invention

An analogous sample of PS, for composition, geometry and absence of the barrier film, to that described in Example 7, was housed in the reactor of the batch foaming apparatus illustrated in FIG. 1 and previously described at room temperature. The reactor was then closed and brought to a temperature of 100° C.

The system was then subjected to the solubilisation phase of the expanding $CO_2$ and $N_2$ gas using the pressure profile described in Table 8.

TABLE 8

|  | Initial pressure (bars) | Final pressure (bars) | Duration (minutes) |
|---|---|---|---|
| Step 1 | 0 | 100 ($CO_2$) | 0.2 |
| Step 2 | 100 ($CO_2$) | 100 ($CO_2$) | 10 |
| Step 3 | 100 ($CO_2$) | 100 ($N_2$) | 0.2 |
| Step 4 | 100 ($N_2$) | 100 ($N_2$) | 0.5 |

As shown in Table 8, the pressure profile comprised four phases:

in step 1, the pressure of the expanding $CO_2$ gas was brought from atmospheric pressure to 100 bars with a linear ramp in 0.2 minutes (12 seconds);

in step 2, the expanding $CO_2$ gas pressure was kept at 100 bars for 10 minutes to allow the complete solubilisation of the foaming agent.

in step 3 the $CO_2$ was exchanged with $N_2$ in step 4, the pressure of the expanding $N_2$ gas was kept at 100 bars for 0.5 minutes.

At the end of step 4 the pressure was instantaneously released (at a maximum speed of 1000 bars/s) for foaming.

Figure 9A:
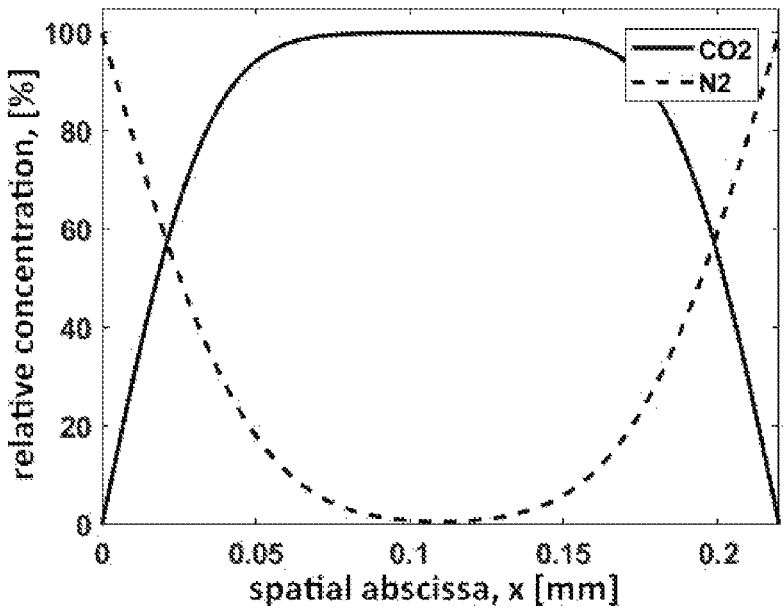
FIG. 9A shows the axial concentration profile of the foaming agent immediately prior to the release of pressure to allow the foaming used in example 8.

Immediately before the release of pressure, at the end of step 2, the concentration profile of the two gases is shown in FIG. 9A.

From this concentration profile, with the release of pressure there was a bimodal foaming, both in terms of density and in terms of morphology.

Figure 9B:
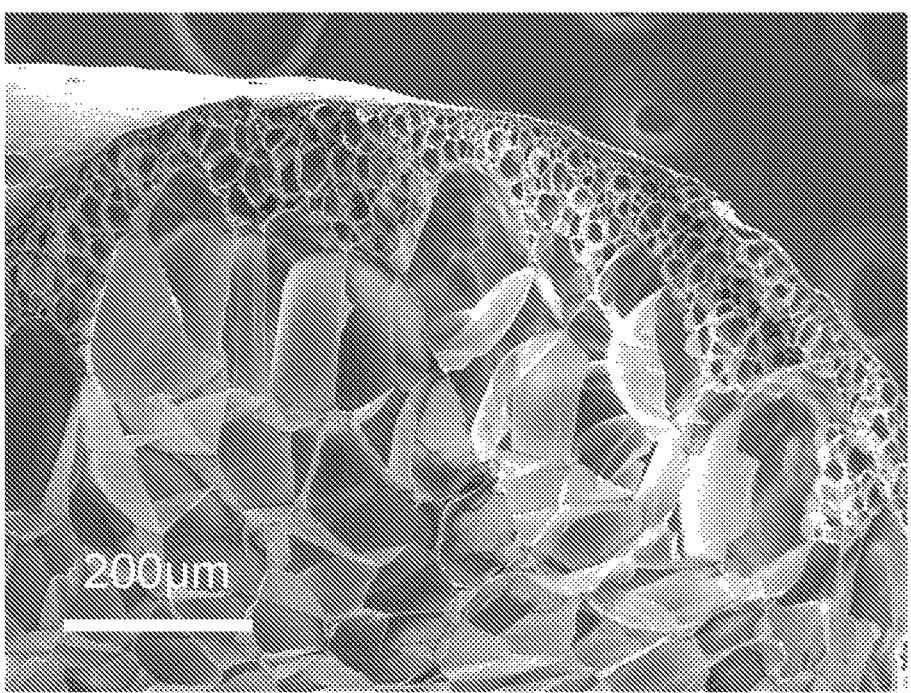
FIG. 9B shows a scanning electron microscope photograph of the foam section resulting from the sample subjected to the procedure of example 8 (scale bar equal to 200 μm).

A scanned electron microscope image of the resulting foam is shown in FIG. 9B. In particular, note how in the outer layers the morphology is very fine, having been foamed using $N_2$ as a foaming agent, while in the central area foamed with $CO_2$, the bubble density is lower. In literature it has been widely proved that $N_2$ has a greater nucleating power than $CO_2$, despite the lower concentration (at the same pressure), which determines lower densities in the case of the use of $CO_2$.

Example 9—Invention

An analogous sample of PS, for composition, geometry and absence of the barrier film, to that described in Example 7, was housed in the reactor of the batch foaming apparatus illustrated in FIG. 1 and previously described at room temperature. The reactor was then closed and brought to a temperature of 100° C.

The system was then subjected to the solubilisation step of the expanding $CO_2$ and 134a (1,1,1,2-tetrafluoroethane) gas using the pressure profile described in Table 9.

TABLE 9

|  | Initial pressure (bars) | Final pressure (bars) | Duration (minutes) |
|---|---|---|---|
| Step 1 | 0 | 100 ($CO_2$) | 0.2 |
| Step 2 | 100 ($CO_2$) | 100 ($CO_2$) | 10 |
| Step 3 | 100 ($CO_2$) | 100 (134a) | 0.2 |
| Step 4 | 100 (134a) | 100 (134a) | 2 |

As shown in Table 1, the pressure profile comprised four phases:

in step 1, the pressure of the expanding $CO_2$ gas was brought from atmospheric pressure to 100 bars with a linear ramp in 0.2 minutes (12 seconds);

in step 2, the expanding $CO_2$ gas pressure was kept at 100 bars for 10 minutes to allow the complete solubilisation of the foaming agent;

in step 3 the $CO_2$ was exchanged with another gas (134a);

in step 4, the expanding 134a gas pressure was kept at 100 bars for 2 minutes.

At the end of step 4 the pressure was instantaneously released (at a maximum speed of 1000 bars/s) for foaming.

Figure 10A:
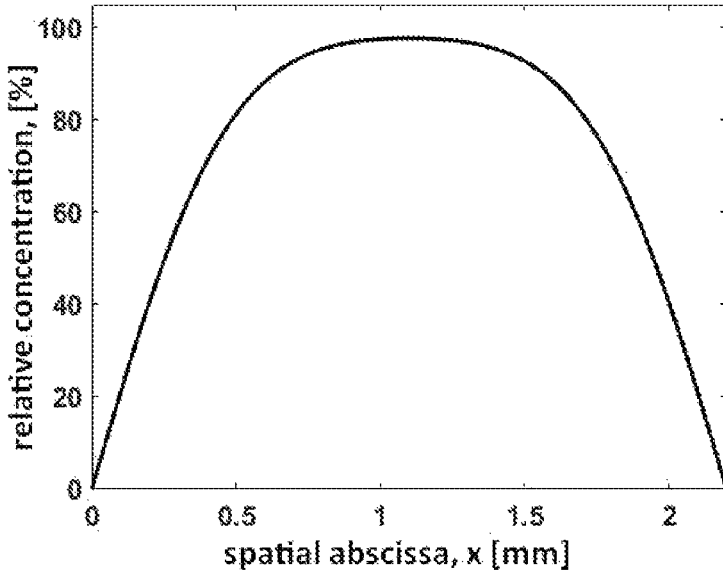
FIG. 10A shows the axial concentration profile of the foaming agent immediately prior to the release of pressure to allow the foaming used in example 9.

Immediately before the release of pressure, at the end of step 2, the concentration profile of the two gases is shown in FIG. 10A.

From this concentration profile, at the release of pressure, foaming was only found in the central layer.

Figure 10B:
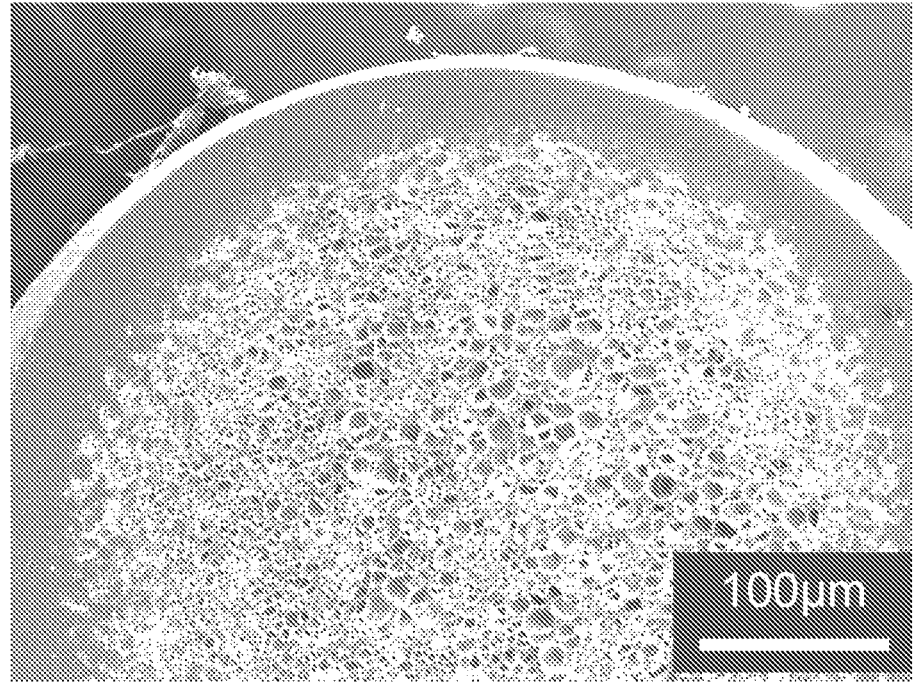
FIG. 10B shows a scanning electron microscope photograph of the foam section resulting from the sample subjected to the procedure of example 9 (scale bar equal to 100 μm).

A scanned electron microscope image of the resulting foam is shown in FIG. 10B. In particular, it is noted how there exists an outer layer of about 50 micrometres, not foamed, and then a foamed inner core. This morphology cannot be obtained except by varying the saturation conditions.

Example 10—Invention

An analogous sample of PS, for composition, geometry and positioning of the barrier film, to that described in Example 1, was coated on one of the two base surfaces (the surface Σ of FIG. 2A), with a polymeric film of poly(vinyl alcohol), PVA, 100 microns thick. This polymer has a carbon dioxide diffusivity of about two orders of magnitude lower than those of the polystyrene in question and can be effectively used to obtain an unsymmetrical concentration profile with respect to the plane, parallel to the base planes, of the centre line of the cylindrical sample. This sample was housed in the reactor of the batch foaming system illustrated in FIG. 1 and previously described at room temperature. The reactor was then closed and brought to a temperature of 100° C.

The system was then subjected to the solubilisation step of the expanding $CO_2$ gas using the pressure profile described in Table 10.

TABLE 10

|  | Initial pressure (bars) | Final pressure (bars) | Duration (minutes) |
|---|---|---|---|
| Step 1 | 0 | 130 ($CO_2$) | 0.2 |
| Step 2 | 130 ($CO_2$) | 130 ($CO_2$) | 600 |
| Step 3 | 130 ($CO_2$) | 80 ($CO_2$) | 10 |
| Step 4 | 80 ($CO_2$) | 130 ($CO_2$) | 10 |

As shown in Table 10, the pressure profile comprised four phases:

in step 1, the pressure of the expanding $CO_2$ gas was brought from atmospheric pressure to 130 bars with a linear ramp in 0.2 minutes (12 seconds);

in step 2, the expanding $CO_2$ gas pressure was kept at 130 bars for 10 hours (600 minutes) to allow the complete solubilisation of the foaming agent;

in step 3, the pressure of the expanding $CO_2$ gas was decreased to 80 bars with a linear ramp in 10 minutes;

in step 4, the pressure of the expanding $CO_2$ gas was increased to 130 bars with a linear ramp in 10 minutes.

At the end of step 4 the pressure was instantaneously released (at a maximum speed of 1000 bars/s) for foaming.

Immediately before the release of pressure, at the end of step 2, the concentration profile of the two gases is shown in FIG. 11A.

From this concentration profile, upon the release of pressure, the different foaming capacities of the different areas were found.

The areas with a high concentration of foaming agent were more foamed with a morphology and density depending on the foaming conditions, while the areas with a low concentration of foaming agent were less foamed.

Figure 11C:
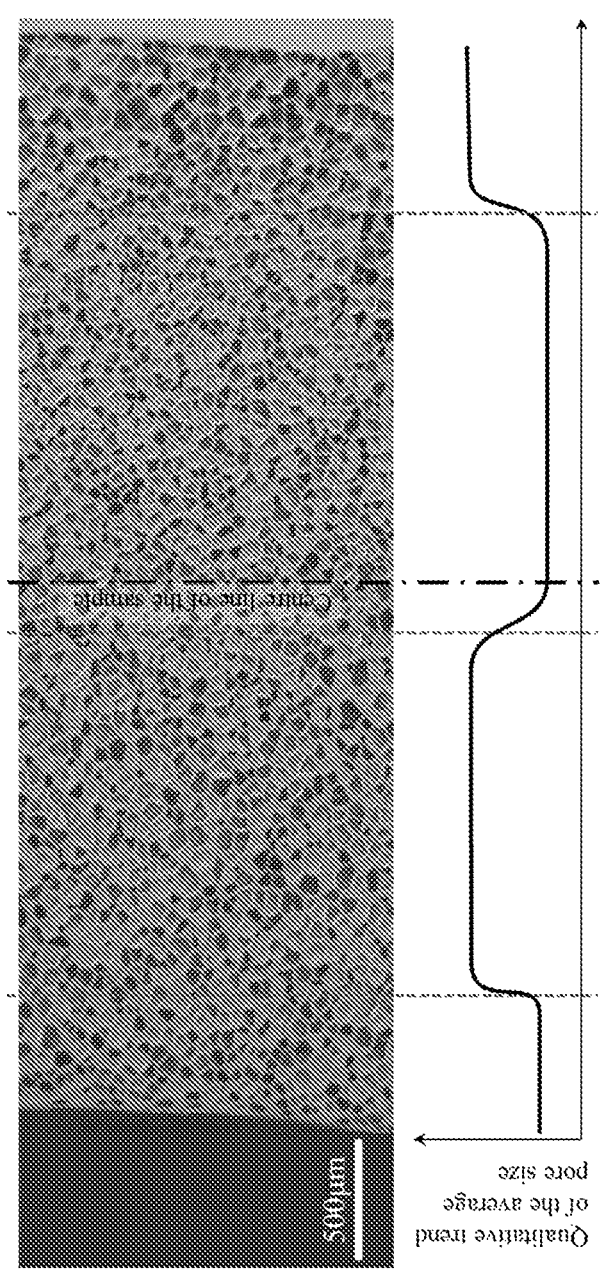
FIG. 11C shows the same scanning electron microscope photograph of FIG. 11B wherein a diagram has been inserted that shows the qualitative trend of the pore size at the different areas of the SEM micrograph, and the vertical dotted lines outline the different areas.

In particular, FIG. 11B shows a scanned electron microscope image of a section of the foam produced, with an evident unsymmetrical four-layer structure with respect to the centre of the sample (indicated in the image in FIG. 11C as the "centre line of the sample"). To guide the eye, a diagram has been inserted that shows the qualitative trend of the pore size at the different areas of the SEM micrograph. The vertical dotted lines outline the different areas.

Example 11—Invention

Figure 12A:
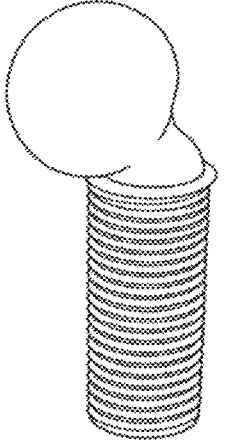
FIG. 12A shows a porous metal container having the shape of the upper end portion of the femur used in example 11.

A sample of polycaprolactone, PCL, a biocompatible polyester used in the field of tissue engineering, was introduced into a porous metal container having the shape of the upper end portion of the femur, illustrated in FIG. 12A, so as to limit and shape the foamed material, and the container was housed in the reactor of the batch foaming apparatus illustrated in FIG. 1 and previously described at room temperature. The reactor was then closed and brought to a temperature of 80° C. for 5 minutes and then to 60° C.

The system was then subjected to the solubilisation phase of the expanding $CO_2$ and $N_2$ gas using the pressure profile described in Table 11.

TABLE 11

| | Initial pressure (bars) | Final pressure (bars) | Duration (minutes) |
|---|---|---|---|
| Step 1 | 0 | 100 ($CO_2$) | 0.2 |
| Step 2 | 100 ($CO_2$) | 100 ($CO_2$) | 600 |
| Step 3 | 100 ($CO_2$) | 100 ($N_2$) | 0.2 |
| Step 4 | 100 ($N_2$) | 100 ($N_2$) | 3 |

As shown in Table 8, the pressure profile comprised four phases:

in step 1, the pressure of the expanding $CO_2$ gas was brought from atmospheric pressure to 100 bars with a linear ramp in 0.2 minutes (12 seconds);

in step 2, the expanding $CO_2$ gas pressure was kept at 100 bars for 10 minutes to allow the complete solubilisation of the foaming agent.

in step 3 the $CO_2$ was exchanged with $N_2$ in step 4, the pressure of the expanding $N_2$ gas was kept at 100 bars for 3 minutes.

During step 4, the temperature was brought to 40° C., and at the end of step 4 the pressure was instantaneously released (at a maximum speed of 1000 bars/s) for the foaming.

Immediately before the release of pressure, at the end of step 4, the concentration profile of the two gases was similar to that shown in FIG. 9A.

From this concentration profile, with the release of pressure there was a dual foaming, both in terms of density and in terms of morphology.

Figure 12B:
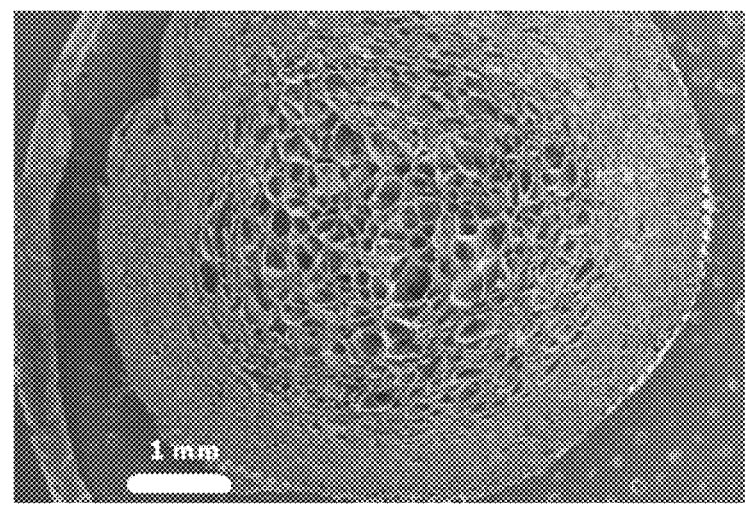
FIG. 12B shows a scanning electron microscope photograph of the longitudinal foam section resulting from the sample subjected to the procedure of example 11 (scale bar equal to 1 mm).
Figure 12C:
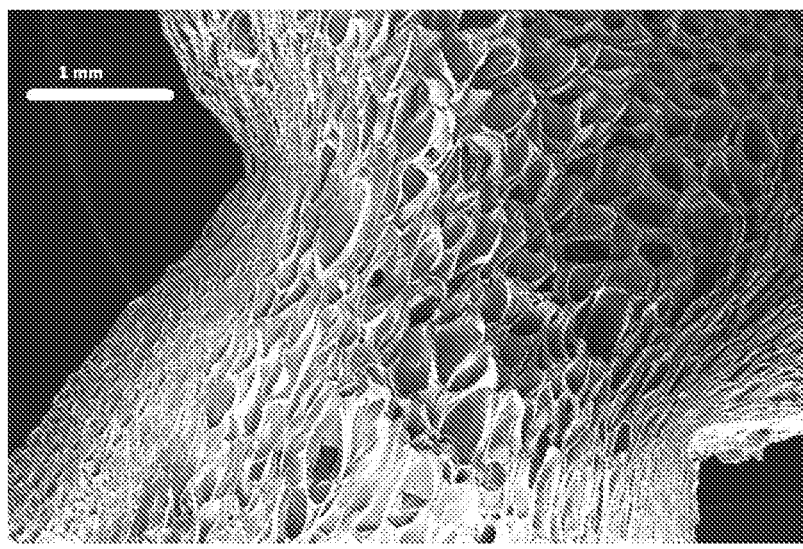
FIG. 12C shows a scanning electron microscope photograph of the transversal foam section resulting from the sample subjected to the procedure of example 11 (scale bar equal to 1 mm).
Figure 12D:
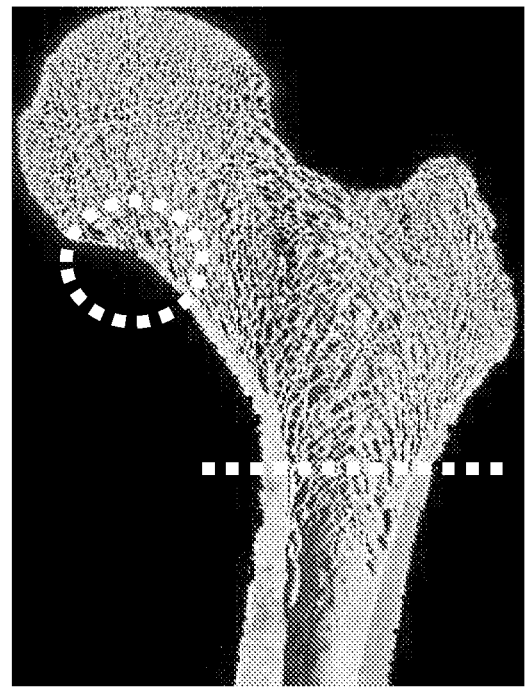
FIG. 12D shows a transversal section of the head of a femur.

A scanned electron microscope image of the resulting foam is shown in FIGS. 12B and 12C. FIG. 12B illustrates a longitudinal section, while FIG. 12C illustrates a transversal section. The similarity with the bone structure of the femur, illustrated in FIG. 12D, is surprising. In particular, the straight dotted line of FIG. 12D indicates an area of the actual femur structure which is very similar to that shown in FIG. 12B of the foamed sample, while the circular line of FIG. 12D indicates an area of the actual femur structure which is very similar to that shown in FIG. 12C of the foamed sample. Note the orientation and the elongated pore shape in FIG. 12C, just like in an actual femur, obtained during the filling of the mould (the pores follow the flow lines of the polymer during the foaming phase).

With the process of the present invention it is therefore possible to create artificial bone prostheses easily and at a low cost. In general, by appropriately designing the mould, the level of polymer filling, the solubilisation steps and the fluid dynamics of the mould filling of the polymer during the foaming, it is possible to create multi-gradient porous structures with the desired cell morphologies, densities and orientations, optimizing the structural and functional anisotropic properties of the foamed material.

The invention claimed is:

1. A process for preparing a layered foamed polymeric material with one or more foaming agents, where said method comprises:

providing a foamable polymeric material in a closed reactor and raising the pressure of the one or more foaming agents into the closed reactor up to a maximum of 300 bars;

solubilising said one or more foaming agents in the foamable polymeric material under pressure and at a temperature greater than 20° C.; and releasing the pressure instantaneously;

wherein said solubilising is carried out with a pressure profile of said one or more foaming agents that is variable over time, wherein said pressure profile which is variable over time in said solubilising of said one or more foaming agents in said foamable polymeric material generates a non-uniform profile of the concentrations of said one or more foaming agents in said foamable polymer, which upon foaming correspondingly generates a non-uniform morphology and density in said foamed polymeric material and wherein said pressure profile varies from a minimum pressure equal to atmospheric pressure to a maximum of 300 bars.

2. The process according to claim 1, wherein said pressure profile varies over time in a periodic or non-periodic manner.

3. The process according to claim 2, wherein said pressure profile varies over time in a periodic manner with a waveform selected from the group consisting of the sinusoidal, triangular, square or sawtooth type, or combinations thereof.

4. The process according to claim 2, wherein said pressure profile varies over time in a non-periodic manner following a linear, sectioned, curvilinear, parabolic, exponential, impulsive profile, or combinations thereof.

5. The process according to claim 1, wherein said pressure profile comprises at least one step with a pressure profile increasing over time and at least one step with a pressure profile decreasing over time.

6. The process according to claim 5, wherein said pressure profile comprises at least one step with a constant pressure profile over time.

7. The process according to claim 1, wherein one foaming agent is used.

8. The process according to claim 1, wherein a mixture of two or more foaming agents is used.

9. The process according to claim 8, wherein the concentration of said foaming agents in said mixture varies over time.

10. The process according to claim 1, wherein said one or more foaming agents is selected from the group consisting of an inert gas, carbon dioxide, and a substituted or not substituted aliphatic hydrocarbon (linear, branched or cyclic), having from 3 to 8 carbon atoms.

11. The process according to claim 10, wherein said one or more foaming agents is selected from the group consisting of nitrogen, carbon dioxide, n-butane, iso-butane, n-pentane, iso-pentane, 1,1,1,2-tetrafluoroethane (Freon R-134a), 1,1-difluoroethane (Freon R-152a), difluoromethane (Freon R-32), and pentafluoroethane.

12. The process according to claim 1, wherein said foamable polymeric material is selected from the group consisting of a thermoplastic polymeric material and a thermosetting polymeric material.

13. The process according to claim 12, wherein said thermoplastic polymeric material is selected from the group consisting of a polyolefin, a polyurethane, a polyester and a polyamide.

14. The process according to claim 12, wherein said thermosetting polymeric material is selected from the group consisting of a polyurethane, an epoxy resin, a melamine resin, a polyphenol, and a polyimide.

\* \* \* \* \*